(12) United States Patent
Rincon et al.

(10) Patent No.: US 11,020,255 B2
(45) Date of Patent: Jun. 1, 2021

(54) APPARATUS FOR AND METHOD OF PULLING A TENSILE MEMBER FROM A MEDICAL DEVICE

(75) Inventors: Cesar Rincon, Easton, PA (US); Matthew Krever, Basking Ridge, NJ (US); Daniel Olsen, Califon, NJ (US); Edward Johnson, Skaneateles, NY (US)

(73) Assignee: CARDINAL HEALTH SWITZERLAND 515 GMBH, Bar Zug (CH)

( * ) Notice: Subject to any disclaimer, the term of this patent is extended or adjusted under 35 U.S.C. 154(b) by 25 days.

(21) Appl. No.: 13/260,881

(22) PCT Filed: Jun. 22, 2011

(86) PCT No.: PCT/US2011/041483
§ 371 (c)(1),
(2), (4) Date: Dec. 21, 2012

(87) PCT Pub. No.: WO2011/163386
PCT Pub. Date: Dec. 29, 2011

(65) Prior Publication Data
US 2013/0085562 A1   Apr. 4, 2013

Related U.S. Application Data

(60) Provisional application No. 61/358,197, filed on Jun. 24, 2010.

(51) Int. Cl.
*A61F 2/966* (2013.01)
*A61F 2/95* (2013.01)

(52) U.S. Cl.
CPC ........... *A61F 2/95* (2013.01); *A61F 2/9517* (2020.05); *A61F 2002/9511* (2013.01)

(58) Field of Classification Search
CPC ...... A61F 2002/9665; A61F 2002/9511; A61F 2002/9517; A61F 2/962; A61F 2/966; A61F 2/95–97; A61F 2/2427–2439
(Continued)

(56) References Cited

U.S. PATENT DOCUMENTS 5,236,434 A * 8/1993 Callicrate .................. 606/135
5,591,172 A   1/1997 Bachmann et al.
(Continued)

FOREIGN PATENT DOCUMENTS

| CN | 1732855 A | 2/2006 |
| CN | 1897892 A | 1/2007 |

(Continued)

OTHER PUBLICATIONS

European Search Report for Application No. EP17173586, dated Sep. 6, 2017, 6 pages.
(Continued)

*Primary Examiner* — Kathleen S Holwerda
(74) *Attorney, Agent, or Firm* — Arent Fox

(57) ABSTRACT

Mechanisms for pulling a tensile member a predetermined distance from a medical device having an intracorporeal end and an extracorporeal end are disclosed. Such mechanisms may be safely operated using a robot, two hands, or in some embodiments, only one hand. Such mechanisms may include one or more cams, drums, or pulley-like members and a lever, and may be physically coupled to an extracorporeal portion of the medical device.

51 Claims, 30 Drawing Sheets

(58) Field of Classification Search
USPC .......................... 623/1.11, 1.12; 3/1.11, 1.12
See application file for complete search history.

(56) References Cited

U.S. PATENT DOCUMENTS

| | | | |
|---|---|---|---|
| 5,639,274 | A | 6/1997 | Fischell et al. |
| 5,935,102 | A | 8/1999 | Bowden et al. |
| 5,944,727 | A | 8/1999 | Ahari et al. |
| 5,968,052 | A * | 10/1999 | Sullivan, III ............. A61F 2/95 |
| | | | 606/206 |
| 6,143,021 | A | 11/2000 | Staehle |
| 6,248,128 | B1 | 6/2001 | Berry et al. |
| 6,514,261 | B1 | 2/2003 | Randall et al. |
| 6,530,947 | B1 | 3/2003 | Euteneuer et al. |
| 6,626,913 | B1 | 9/2003 | McKinnon et al. |
| 6,755,854 | B2 | 6/2004 | Gillick et al. |
| 6,872,224 | B1 | 3/2005 | Telxelra Moretra et al. |
| 6,884,259 | B2 | 4/2005 | Tran et al. |
| 7,052,511 | B2 | 5/2006 | Weldon et al. |
| 7,122,050 | B2 | 10/2006 | Randall et al. |
| 7,147,657 | B2 | 12/2006 | Chiang |
| 7,384,426 | B2 | 6/2008 | Wallace et al. |
| 7,556,641 | B2 | 7/2009 | Cully et al. |
| 7,611,528 | B2 * | 11/2009 | Goodson, IV .......... A61F 2/962 |
| | | | 623/1.11 |
| 7,625,387 | B2 | 12/2009 | Wixey |
| 7,632,252 | B2 | 12/2009 | Prais et al. |
| 7,635,382 | B2 | 12/2009 | Pryor |
| 7,637,932 | B2 | 12/2009 | Bolduc et al. |
| 7,763,063 | B2 | 7/2010 | Arbefeuille |
| 7,823,267 | B2 | 11/2010 | Bolduc |
| 8,062,345 | B2 | 11/2011 | Ouellette |
| 8,070,790 | B2 | 12/2011 | Berra |
| 8,080,050 | B2 | 12/2011 | Chiang et al. |
| 8,092,519 | B2 | 1/2012 | Bolduc |
| 8,449,595 | B2 | 5/2013 | Ouellette |
| 8,500,792 | B2 | 8/2013 | Berra |
| 8,690,897 | B2 | 4/2014 | Bolduc |
| 8,771,333 | B2 | 7/2014 | Rincon |
| 9,173,755 | B2 | 11/2015 | Berra |
| 9,220,617 | B2 | 12/2015 | Berra |
| 2002/0077634 | A1 | 6/2002 | Leonhardt et al. |
| 2004/0148008 | A1 * | 7/2004 | Goodson, IV .......... A61F 2/962 |
| | | | 623/1.12 |
| 2004/0148009 | A1 | 7/2004 | Buzzard et al. |
| 2004/0181239 | A1 * | 9/2004 | Dorn ......................... A61F 2/95 |
| | | | 606/108 |
| 2005/0027306 | A1 | 2/2005 | Krivoruchko et al. |
| 2005/0080476 | A1 * | 4/2005 | Gunderson et al. ......... 623/1.11 |
| 2005/0090890 | A1 * | 4/2005 | Wu et al. .................... 623/1.11 |
| 2006/0020287 | A1 * | 1/2006 | Lee et al. ..................... 606/205 |
| 2007/0043381 | A1 * | 2/2007 | Furst ....................... A61F 2/962 |
| | | | 606/108 |
| 2007/0156224 | A1 | 7/2007 | Cioanta et al. |
| 2007/0179586 | A1 | 8/2007 | Aguirre et al. |
| 2007/0219617 | A1 * | 9/2007 | Saint ............................ 623/1.12 |
| 2007/0255390 | A1 * | 11/2007 | Ducke et al. ................ 623/1.11 |
| 2009/0264992 | A1 | 10/2009 | Fleming, III et al. |
| 2009/0270967 | A1 | 10/2009 | Fleming, III et al. |
| 2010/0030255 | A1 | 2/2010 | Berra et al. |
| 2010/0174354 | A1 * | 7/2010 | Hyodoh .................... A61F 2/95 |
| | | | 623/1.11 |
| 2010/0324647 | A1 | 12/2010 | Rincon |
| 2011/0034987 | A1 * | 2/2011 | Kennedy ................... A61F 2/95 |
| | | | 623/1.11 |
| 2011/0288624 | A1 * | 11/2011 | Roeder ..................... A61F 2/07 |
| | | | 623/1.11 |

FOREIGN PATENT DOCUMENTS

| | | |
|---|---|---|
| CN | 2875368 Y | 3/2007 |
| CN | 1961847 A | 5/2007 |
| CN | 201046135 Y | 4/2008 |
| CN | 101754727 A | 6/2010 |
| DE | 19838414 A1 | 3/2000 |
| EP | 0603423 B1 | 9/1997 |
| EP | 1086664 A2 | 3/2001 |
| EP | 1440673 A1 | 7/2004 |
| EP | 1173701 B1 | 9/2006 |
| EP | 1834610 A1 | 9/2007 |
| EP | 1776938 B1 | 5/2009 |
| EP | 1772120 B1 | 8/2011 |
| EP | 2585004 B1 | 5/2017 |
| JP | 200129478 A | 7/1999 |
| JP | 2001506875 A | 5/2001 |
| JP | 2002525168 A | 8/2002 |
| JP | 2005230471 A | 9/2005 |
| JP | 2006502760 A | 1/2006 |
| JP | 2007508045 A | 4/2007 |
| JP | 2007244881 A | 9/2007 |
| JP | WO 2009028272 A1 * | 3/2009 ............... A61F 2/95 |
| JP | 2009528905 A | 8/2009 |
| JP | 2010063816 A | 3/2010 |
| WO | 9823241 A2 | 6/1998 |
| WO | 2007044929 A1 | 4/2007 |
| WO | 2007053233 A2 | 5/2007 |
| WO | 2008034793 A1 | 3/2008 |
| WO | 2009012061 A1 | 1/2009 |
| WO | 2011163386 A1 | 12/2011 |

OTHER PUBLICATIONS

International Search Report and Written Opinion for Application No. PCT/US2011/041483, dated Oct. 14, 2011, 3 pages.

European Office Action mailed in European Patent Application No. 17173586.3, dated Aug. 10, 2018, 5 pages.

European Office Action mailed in European Patent Application No. 17173586.3, dated Feb. 6, 2019, 5 pages.

* cited by examiner

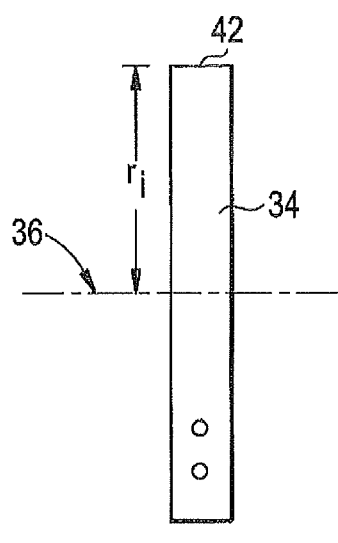
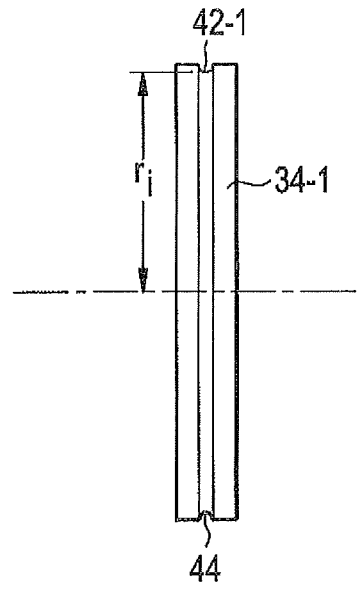
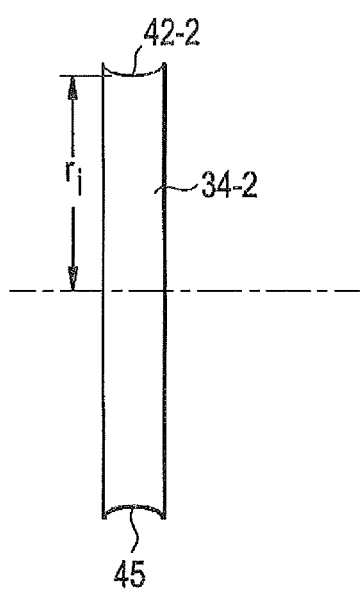

APPARATUS FOR AND METHOD OF PULLING A TENSILE MEMBER FROM A MEDICAL DEVICE

RELATED APPLICATIONS

This application is a National Stage Application of PCT/US2011/041483, filed Jun. 22, 2011, which claims the benefit of priority of U.S. Provisional Patent Application No. 61/358,197, filed Jun. 24, 2010. The complete disclosures of the aforementioned related patent applications are incorporated by reference herein.

BACKGROUND

1. Technical Field

The invention relates to the field of medical device, and more particularly a hand-operated mechanism for pulling a tensile member from a medical device.

2. Related Devices and Methods

Vascular disease is a leading cause of premature mortality in developed nations. Treatment of vascular disease may include implantation of tissue supporting stents or prosthetic vasculature, e.g., grafts, stent-grafts, etc., which are delivered through the vasculature at a reduced dimension for ease of navigation in, and reduced chance of injury to, the tortuous vasculature from entry point to the diseased location. These vascular implant delivery devices typically include an elongated shaft around which the vascular implant is disposed at a distal end, which is the end furthest from the medical professional implanting the vascular implant. Such shafts may have variable designs as best suited to deliver the vascular implant from the point of entry to the vasculature to the intended implantation site. Some delivery devices further include additional features such as soft tips on the distal ends of the elongated shafts, sheaths or outer members disposed about much of the length of the elongated shaft and about the vascular implant, and various features on the proximal end, which is the end closest to the medical professional to perform varied functions, e.g., release of dye or other visualization agent, valved access to a lumen running through the elongated shaft for inserting a guide wire, sealed attachment of a pressurized fluid to inflate balloons at the distal end, or other mechanisms involved in the controlled delivery of the vasculature to its intended site. This disclosure describes an extracorporeal mechanism by which to pull a tensile member from a medical device and methods of operating the mechanism or otherwise pulling the tensile member from the medical device. Unless otherwise stated, the other variations in the construction of the medical device to which the present invention is coupled or is otherwise a physical part of are not germane to the present invention.

Certain vascular implant delivery devices retain one or more members of a self expanding vascular implant at a smaller dimension until the retaining mechanism is disengaged from the one or more members. Examples of some of these devices are described in U.S. Pat. Pub. Nos. 2009/0264992 A1 and 2009/0270967 A1, as well as U.S. patent application Ser. No. 12/489,738, filed on Jun. 23, 2009. This retaining mechanism may be a part of a more complex securement and release device, or it may be a same part that alternatively functions to release the part (e.g., one or more hoop or hook) with which it is engaged, and would otherwise be called a release mechanism. In some designs of the securement and release device, to deploy the distal end of the vascular implant, a tensile member that is attached to a part of the device that retains a set of hoops of the vascular implant must move in a direction parallel to the longitudinal axis of the vasculature within which the vascular implant is to be deployed. Some designs of the device require that the tensile member be pulled away from the distal end, or in other words, in the opposite direction. The tensile member must be pulled a first predetermined distance to move the part of the device to which it is attached a second predetermined distance. If the tensile member does not lengthen or stretch while being pulled, and the components of the delivery device connecting between the point of attachment of the tensile load from the tensile member and the point of application of the stabilizing force by the medical professional external to the patient do not compress (and shorten) under the compressive load, those distances are equal. Alternatively or additionally, moving the tensile member a predetermined distance could work to actuate a release mechanism by means other than moving a separate part, such as, for example, untying a knot and thereby removing a retaining force provided by the knotted or otherwise secured tensile member, such as a wire.

In many cases, the medical device is an elongated device, and the tensile member extends from its point of attachment to the release mechanism within and/or along a length of the elongated device to a point external to the device and patient. The tensile member does not require a mechanism to pull it, as an operator of the medical device can simply grasp the extracorporeal portion of the tensile member in one hand and an extracorporeal end of the medical device in the other and apply a force to the tensile member in the proximal direction and an equal and opposing force to the extracorporeal end of the medical device. Of course, if the operator of the medical device is using a robot to pull the tensile member, the operator would grasp the extracorporeal portion of the tensile member with one end effector of the robot and the extra corporeal end of the medical device in second end effector of the robot, and then apply a force to the tensile member in the proximal direction and an equal and opposing force to the extracorporeal end of the medical device. However, regardless whether it is hand operated or robotically operated, if the force required to move the tensile member and optional release mechanism is applied in the proximal direction, and the movement of the mechanism is with respect to other portions of the medical device, a chance exists that an operator will apply a force in the proximal or distal direction to the other portions of the medical device and move it in an unintended fashion. When the medical device is a vascular implant delivery device, such forces may move the elongated shaft and the coupled implant axially as it is being deployed, resulting in an inaccurate placement of the implant in the vasculature.

SUMMARY

An embodiment of a vascular implant delivery device includes an elongated shaft having a distal end, a proximal end, and a longitudinal axis. The device also has a release mechanism and a tensile member coupled to the release mechanism at a first point along its length and to an extracorporeal member at a second point along its length. The device also includes mechanical means operable with one hand for pulling the tensile member with respect to the elongated shaft, which moves the release mechanism toward the proximal end of the elongated shaft. The mechanical means includes the extracorporeal member, and optionally includes: a cam for a length of the tensile member between the first point and the second point, wherein the cam is coupled to the elongated shaft, a lever rotatably coupled to the elongated shaft, and a grip coupled to and in a fixed position with respect to a portion of the elongated shaft, the grip adapted to receive forces from one or more digits of the one hand, wherein either the lever or the cam is the extracorporeal member.

An embodiment of a vascular implant delivery device includes an elongated shaft having a distal end, a proximal end, and a longitudinal axis. The device also includes a release mechanism, a lever rotatably coupled to the elongated shaft, a tensile member coupled to the release mechanism at a first point along its length and coupled to the lever at a second point along its length and a length of the tensile member between the first and second points disposed within the elongated shaft, and a cam for a length of the tensile member between the first point and the second point, the cam coupled to the elongated shaft, wherein the lever, cam, and tensile member are adapted to cooperate such that rotation of the lever through a prescribed angle with respect to the elongated shaft will move the release mechanism toward the proximal end of the elongated shaft.

These and other features, benefits, and advantages of the present invention will be made apparent with reference to the following detailed description, appended claims, and accompanying figures, wherein like reference numerals refer to structures that are either the same structures, or perform the same functions as other structures, across the several views.

BRIEF DESCRIPTION OF THE FIGURES

The figures are merely exemplary and are not meant to limit the present invention.

FIGS. 3A, 3B, and 3C illustrate end views of a cam having surface intended for contact with the tensile member.

DETAILED DESCRIPTION

Figure 1:
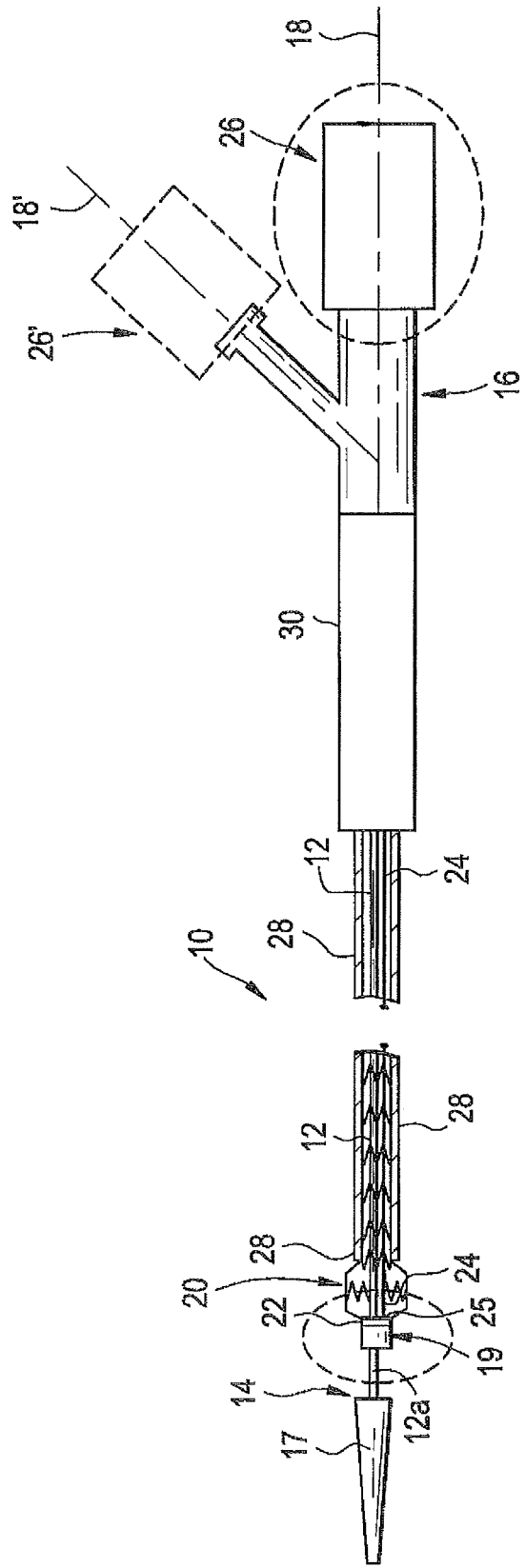
FIG. 1 illustrates an elongated shaft equipped with a release mechanism, a tensile member, and an apparatus for pulling the tensile member toward the proximal end of the elongated shaft.

The apparatus for pulling a tensile member is coupled to a medical device, and when physically coupled to the medical device, is considered a part of the medical device. That is to be kept in mind when the apparatus is described as being coupled to the proximal end of the medical device, as the reference to a depicted "proximal end" of a medical device to which the apparatus is physically coupled is one of convenience, recognizing that the medical device may include other mechanisms added by way of intervening mountings between the proximal end of an elongated shaft portion of the medical device and the mounting through which the apparatus for pulling wire is physically connected to the remainder of the medical device.

For embodiments of medical devices which are elongated, these elongated devices have one or more longitudinal axes. If a Y connector is added to an elongated device such that a secondary longitudinal axis is created, that secondary longitudinal axis in combination with the distal portion of the first longitudinal axis (through the main device) is considered herein for the purposes of this disclosure as the longitudinal axis of the device, if the tensile member runs co-axial with or along side such secondary longitudinal axis for a distance. In the drawings, these secondary (or tertiary, etc.) longitudinal axes are indicated by the inclusion of a ' (or more than one ') after the corresponding identifying numeral. In other words they are identified as prime (or double or triple prime, etc.).

The terms "tube" and "tubular" are used in their broadest sense, that is, any object which is arranged at a radial distance about a longitudinal axis. Accordingly, the terms "tube" or "tubular" include any structure that is (i) cylindrical or not, such as for example having an elliptical or polygonal transverse cross-section, or any other regular or irregular cross-section; (ii) has a changing or different cross-section along its length; (iii) is arranged around a straight, curved, bent, or discontinuous axis; (iv) has an imperforate, or a periodic or other perforate, irregular, or gapped surface or cross-section; (v) is spaced uniformly or irregularly, including being spaced varying radial distances from the longitudinal axis; or (vi) has any desired length or cross-sectional size.

The term "lever" is used herein to refer to a rigid body, i.e., one with negligible bending to serve its purpose, that is used with a fulcrum or about a pivotal axis, to transmit a force applied to the lever at a first point (an "applied force") to a body (load) in contact with a second point (a "transmitted force") or to transmit a force proportional to the applied force to a body (load) in contact with a second point (a "modified force"). The relative position with respect to the lever of the fulcrum, the applied force, and the modified or transmitted force may vary. In a first class of levers, the fulcrum or pivotal axis is between the applied force and the modified or transmitted force. In a second class of levers, the modified force is between the fulcrum or pivotal axis and the applied force. In a third class of levers, the applied force is between the fulcrum and the modified force.

The term "coupled" and other conjugations or noun forms shall include connections between two physical parts (a first part and a second part) that are either direct or indirect, i.e., through a series of direct connections between the first part and the first of a plurality of intervening members and between the last of the plurality of intervening members and the second part, and where those connections may be either mechanical or non-mechanical, e.g., electromagnetic energy couplings, magnetic couplings. Rube Goldberg machines are an extreme example of indirect connections between a "coupled" input member and the final output member.

The term "connected" and other conjugations or noun forms shall mean direct mechanical connections. Removable physical contact between parts is a direct connection. Thus, e.g., with reference to FIG. 1, tip 17 is coupled (and connected) to the distal end 12a of shaft 12, but tip 17 is only coupled to tensile member 24. The series of direct connections in the coupling between tip 17 and tensile member 24 in FIG. 1 is as follows: tip 17 is connected to inner member 15; inner member 15 is connected to securement and release mechanism 19 of which release member 22 is a part; release member 22 is connected to tensile member 24.

Cam Variations

In this section, the inventors describe variations of an apparatus for pulling the tensile member that have at least one cam, as the term is used herein.

In some embodiments, the cam is rotatable with respect to the device. In some embodiments of a rotatable cam, the tensile member and the cam rotate together without relative motion between the cam surface and the tensile member. In some embodiments of a rotatable cam, the tensile member and cam move relative to one another. In some embodiments of a rotatable cam, the tensile member and cam sometimes rotate together and sometimes move relative to one another. In some embodiments of a rotatable cam, the relative motion of the tensile member and cam surface generates friction between the tensile member and the cam surface.

In some embodiments, the cam is in a fixed position with respect to the device. In some embodiments of a fixed cam, the tensile member moves relative to the cam surface. In some embodiments of a fixed cam, the tensile member slides on the cam surface. In some embodiments of a fixed cam, the relative motion of the tensile member and cam surface generates friction between the tensile member and the cam surface.

In some embodiments of a rotatable cam, the surface of the cam in contact with the tensile member has a constant distance from the axis of cam rotation. In these embodiments, the cam may act as a pulley, if the cam is substantially cylindrical in shape. A substantially cylindrical cam may have a groove between two flanges, as typical pulleys do.

In embodiments where the tensile member is wound around a rotatable cam at least about 360° (three hundred and sixty degrees) during rotation of the rotatable cam, and that surface in contact with the added tensile member is at a constant distance from the axis of cam rotation, the cam may be called a drum, such as a drum used in a winch.

In some embodiments of a rotatable cam, the surface of the cam in contact with the tensile member has a variable distance from the axis of cam rotation. In some embodiments of a rotatable cam, the surface of the cam in contact with the tensile member has an increasing distance, r, from the axis of cam rotation as a function of theta, $\theta$, in polar coordinates. In some embodiments of a rotatable cam, the surface of the cam in contact with the tensile member has a constantly increasing distance, r, from $r_i$ at $theta_1$, $\theta_1$, to $r_f$ at $theta_2$, $\theta_2$, in polar coordinates, from the axis of cam rotation.

In some embodiments, the surface of the cam in contact with the tensile member has a constant distance from the axis of lever rotation. In some embodiments, the surface of the cam in contact with the tensile member has a variable distance from the axis of lever rotation. In some embodiments of a cam, the surface of the cam in contact with the tensile member has an increasing distance, r, from the axis of lever rotation as a function of theta, $\theta$, in polar coordinates. In some embodiments of a cam, the surface of the cam in contact with the tensile member has a constantly increasing distance, r, from $r_i$ at $theta_1$, $\theta_1$, to $r_f$ at $theta_2$, $\theta_2$, in polar coordinates, from the axis of lever rotation.

In some embodiments, a cross section of the surface of the cam that is intended to contact the tensile member may be straight. In some embodiments, a cross section of the surface of the cam that is intended to contact the tensile member may match the transverse cross section of the tensile member. In some embodiments, a cross section of the surface of the cam that is intended to contact the tensile member may have the same shape as the transverse cross section of the tensile member, but a larger size. In some embodiments, the surface of the cam intended to contact the tensile member may have a radius equal to or greater than one-half the diameter of a constant diameter tensile member.

In some embodiments, a cross-section of the surface of the cam that is intended to receive the tensile member may be straight. In some embodiments, a cross-section of the surface of the cam that is intended to receive the tensile member may match the transverse cross section of the tensile member. In some embodiments, a cross section of the surface of the cam that is intended to receive the tensile member may have the same shape as the transverse cross section of the tensile member, but a larger size. In some embodiments, a cross section of the surface of the cam intended to receive the tensile member may have a radius equal to or greater than one-half the diameter of a constant diameter tensile member.

In some embodiments, the cam may be continuously in contact with the tensile member from the first point of contact to the last. In some embodiments, the cam may be intermittently in contact with the tensile member between the first point and the last.

Devices with Two Cams

In some embodiments, the device may have two cams. In some embodiments of device having two cams, if the lever is rotated in a first direction, the tensile member contacts the first cam and if the lever is rotated in a second direction, the tensile member contacts the second cam. In some embodiments, the first cam has a first profile and the second cam has a second profile which is a mirror image of the first profile. In some embodiments, the first cam has a first profile, which results in a first amount of tensile member being pulled, and the second cam has a second profile, which results in a different amount of tensile member being pulled than the first amount. In some embodiments, the first cam has a profile that requires a smaller force to rotate the lever past it than the force required to rotate the lever past the second cam.

Tensile Member Variations

The term "tensile member" is used herein to encompass a generally linear body that has a dimension in one of the three orthogonal directions (x, y, z) far exceeding its dimension in the other two and which is intended to be placed in tension, but cannot carry substantial compressive loads without buckling. Substantial compressive loads are those approximately equal in magnitude to the intended tensile load for a tension member, and may include as little as 60% of the intended tensile load. The transverse cross section of a tensile member may have any desired shape, and need not necessarily be circular. A non-limiting example of a tensile member with a non-circular transverse cross section is a filament, formed similarly to tape-flat and relatively thin. The tensile member may be entirely made from metal, plastic, polymer, natural plant fiber, natural animal material, a homogeneous composite material, or a heterogeneous composite material. The tensile member may be entirely made from a combination of materials. A non-limiting example of a tensile member made from a combination of materials is a metal wire having a coating of a polymer on its outer surface. Another non-limiting example of a tensile member made from a combination of materials is a braided or woven tensile member wherein one of the strands woven or braided is metallic and another is polymeric. The tensile member may have a woven or braided construction. The tensile member may be tapered along one or more sections of its length. The tensile member may have a constant transverse cross section along its length. The tensile member may be hollow. A non-limiting example of a tensile member that is hollow is a fine hypotube. The tensile member may be generally solid. A tensile member's construction may vary or be constant along its length. A tensile member's construction may vary or be constant along a path from its longitudinal axis to its outer surface. A tensile member's composition may vary or be constant along its length. A tensile member's composition may vary or be constant along a path from its longitudinal axis to its outer surface.

In some embodiments, a tensile member is more flexible than the elongated shaft of the device of which it is a part.

In some embodiments, elongation of the tensile member at loads expected to be required for actuation of a mechanism via an extracorporeal end of a device should be substantially less than the amount of displacement needed to actuate the mechanism.

In some embodiments, the minimum tensile strength of the tensile member is greater than the loads required for actuation of a mechanism plus a safety factor.

In some embodiments, a tensile member exhibits kink resistance. In some embodiments, a tensile member is able to avoid kinking at radii larger than ~5 mm.

In some embodiments, a tensile member exhibits a generally smooth, lower friction outer surface to reduce the load required to move the tensile member against bodies in which it comes into contact between the point of attachment to the release mechanism and a more proximal portion.

In some embodiments, a tensile member may be a wire. A wire shall mean a generally linear body that has a dimension in one of the three orthogonal directions (x, y, z) far exceeding its dimension in the other two, where the composition is mostly metallic.

In some embodiments, a tensile member is a wire having an outer diameter selected from the range of 0.001 inch to 0.040 inch, inclusive. In some embodiments, a tensile member is a 0.010 inch diameter wire. In some embodiments, a tensile member is a 0.013 inch diameter wire. The selection of the diameter may depend on, among other things, space requirements in the medical device or the body lumen within which the device must be advanced in, the tensile strength of the selected material, and the required pull force to move the first point of the tensile member a desired amount by moving the second point of the tensile member during operation of an apparatus to pull a tensile member from a medical device.

In some embodiments, a tensile member has relatively smaller transverse cross sectional dimensions than the elongated shaft within which or along which it runs. In some embodiments, a tensile member has a transverse cross sectional dimension a percentage of a similar transverse cross sectional dimension of an elongated member within which or along which it runs, and that percentage can be up to 40, or up to 30, or up to 20 or up to 10.

Tensile Member Securement Options

In some embodiments, the extracorporeal member defines a concave partial cylindrical surface, within which a cylinder with the tensile member wrapped around more than 180 degrees is held in an interference fit, in that the dimensions of the outer diameter of the cylinder plus two times the transverse dimension of the tensile member is greater than the diameter of the concave partial cylindrical surface which receives the cylinder and wrapped tensile member. By this dimensional difference, the tensile member is secured with respect to the extracorporeal member.

In some embodiments, the extracorporeal member defines a plurality of through-holes, each with a first opening on one surface of the extracorporeal member and a second opening on another surface of the extracorporeal member. The tensile member is secured to the extracorporeal member by being threaded or stitched through the plurality of through-holes. In some embodiments, the first and second openings are circular and the through-holes are cylindrical.

In some embodiments, the tensile member is tied to the extracorporeal member with one or more knots.

In some embodiments, the tensile member may be secured to the extracorporeal member with one or more crimping disks.

In some embodiments, the tensile member may be secured to the extracorporeal member with any one or more methods of welding.

In some embodiments, the tensile member may be secured to the extracorporeal member with any one or more selected adhesives.

In some embodiments, the tensile member may be secured to the extracorporeal member or other body by being insert-molded.

In some embodiments, the tensile member may be secured to the extracorporeal member or other body with one or more crimp tubes.

In some embodiments, the tensile member may be secured to the extracorporeal member or other body via a threaded screw/nut connection.

Other Aspects of the Tensile Member

Disposing the second end of the tensile member in an internal portion of the device or tensile member pull apparatus removes it from the environment where an operator's gloved hands and fingers are moving, reducing the risk of catching, tearing, and/or puncturing the gloves and/or skin within the gloves. Reducing the risk of glove damage is desirable during medical procedures, especially when blood or other bodily fluids are in the working environment.

Embodiments for One Handed Operation

Desirably, a tensile member pull apparatus consistent with the invention may be held in and operable by one-hand. In these embodiments, fingers of the hand apply the opposing force(s) necessary to keep the extracorporeal end of the delivery device in a fixed position with respect to the patient, such that the force applied by the edge, tip, pad, or other portion of the thumb to the lever only rotates the lever with respect to the device and does not move the extracorporeal end of the device with respect to the patient. In general, human operators of such devices more often succeed in simultaneously ceasing the application of the force to the lever and the force to the device when the forces are applied within one hand than when they are applied with separate hands. In general, human operators of such devices more often succeed in simultaneously matching the force applied to the device opposing the component of the force applied to the lever when the force is applied by the fingers opposing the thumb applying the force to the lever, than when the force is applied by the other hand. For whatever reason, human feedback systems are often better intrahand than interhand.

In some embodiments, the extracorporeal end of the device has a structural feature, a grip. A grip accommodates at least one finger on each side of the elongated shaft of the extracorporeal end of the device to contact it and apply forces to it. A grip may be sized to accommodate two or more fingers on each side of the elongated shaft of the extracorporeal end of the device. In some embodiments, there may be two grips, each on opposing sides of the elongated shaft, and each having a surface facing the intracorporeal end of the device and generally perpendicular to the longitudinal axis of the tensile member at that point, which may be disposed between the two surfaces. Each of these two grips may be sized to accommodate at least one finger to contact it and apply forces to it.

In some embodiments, the combination of the lever and at least one grip fit in the palm of a human hand. In some embodiments, the combination of the lever and at least one grip fit between the thumb and two fingers of a hand in a curved or cupped configuration. In some embodiments, the lever has a maximum distance from the pivotal axis between about 3 and about 7 cm. In some embodiments, the combination of the lever and at least one grip fit within typical ergonomic limits for the human hand. In some embodiments, the lever has a minimum distance at the points of gripping from the pivotal axis within typical ergonomic limits for the human hand. In some embodiments, the lever has a maximum distance from the pivotal axis between about 1 cm and 3 cm. In some embodiments, the lever has a maximum distance from the pivotal axis between about 3 cm and 5 cm. In some embodiments, the lever has a maximum distance from the pivotal axis between about 4 cm and 5 cm.

It will be easily recognized by one of skill in the art that embodiments designed for hand operation may also be operated robotically using end effectors in the place of hands, or elements of a hand such as the palm, one or more fingers, or a thumb. Any embodiment described herein may also be operated robotically.

Lever Rotation Indicators

It may be desirable to avoid unintended rotation of the lever with respect to the device. Further, if unintended rotation of the lever with respect to the device has occurred, it may be desirable for the operator of the device to have an indication of that unintended rotation. Lastly, it may be desirable to fix the lever in position with respect to the device after rotating the designed number of degrees about the pivotal axis. The following embodiments of the above described apparati may meet one or more of the above desirable features.

In some embodiments, the apparatus includes a ratchet tooth which can deflect a deflectable structure of the lever if that deflectable structure is forced past it during rotation of the lever about the pivotal axis, permitting the lever to rotate past the ratchet tooth in one direction, and preventing the lever from rotating past the ratchet tooth in the opposite direction. In some embodiments, the ratchet tooth is placed in the path of the rotation of the lever close to the point of initiation of rotation. In some embodiments, the ratchet tooth is placed in the path of the lever close to the point of final desired rotation of the lever.

In some embodiments, the ratchet tooth projects from a side surface of the cam and if the deflectable structure is forced past it during rotation of the lever about the pivotal axis, the deflectable structure will deflect away from the cam.

In some embodiments, the extracorporeal end of the device includes a ratchet tooth adjacent the path of an edge of the lever, such that if the lever rotates past the ratchet tooth, the ratchet tooth will be deflected by the lever away from the lever until the lever passes the ratchet tooth.

In some embodiments, the ratchet tooth may project from the lever itself and interfere with a rigid projection from the cam or extracorporeal end of the device.

In some embodiments, a ratchet tooth may have a beveled surface that gradually increases the interference between the rotating member and the stationary member, and then reduces to a non-interference dimension, either as a step function or some other function that inhibits the rotation of the lever in the opposite direction. Either the ratchet tooth may be designed to deflect or the other of the pair of interfering members may be designed to deflect, or in some embodiments, both the ratchet tooth and the other member of the pair of interfering members may be designed to deflect in one rotational direction and not in the other.

Tensile Forces

In some embodiments, the expected force to pull a tensile member from a medical device may be in the 5-15 pound range. In some embodiments, the minimum force to pull a tensile member from a medical device is 10 pounds+/−1 pound. The forces required to be applied by the hand of a medical professional will depend on that force, but will be modified by mechanical advantage, for example, if any. The presence of turns along the pathway of the tensile member between its point of attachment to a mechanism within the patient and its point of attachment to the apparatus will increase the needed forces to move the tensile member at its first point of attachment.

Desired Length to Pull

The length of a tensile member that needs to be pulled from a medical device to perform a desired act intracorporeally may depend on the expected distance the tensile member will lengthen or stretch during application of a tensile force during operation of the apparatus, and the distance the first point of the tensile member needs to move to actuate any mechanism to which it is attached, or to clear (and release) a desired part of the medical device, including any implant to be delivered. In some embodiments described herein, the distance the second point needs to be moved by the apparatus is in the range of one to two inches. In some embodiments, especially those that deliver prosthetic implants for abdominal aortic aneurysms, the distance the point secured to the extracorporeal member of the apparatus needs to move will be less than about half the total distance of the implant being delivered (and thus less than half the distance any corresponding sheath needs to be retracted).

DETAILED DESCRIPTION OF THE FIGURES

Turning now to the embodiments illustrated in the figures, FIG. 1 illustrates a device for delivering an object to a lumen of a body. In particular, FIG. 1 illustrates a device for delivering an implant to the vasculature of a mammal. In greater particularity, FIG. 1 illustrates a device for delivering a self expanding stent to an artery in a mammal. In some embodiments, the self expanding stent is joined to graft material, which in combination forms part of a prosthetic abdominal or thoracic aorta. Such a prosthesis can be used to internally bypass an abdominal or thoracic aortic aneurysm.

In some embodiments of a delivery device as shown in FIG. 1, the device 10 has a distal end 14, a proximal end 16, and a longitudinal axis 18. In use, the distal end 14 is inside the body. Accordingly, that end of the device may be referred to as a corporeal end of the device, regardless of whether it is actually in the body or not. In use, the proximal end 16 remains outside of the body. Accordingly, that end of the device may be referred to as an extracorporeal end, regardless of whether the device is partially in the body. Device 10 includes a shaft 12, which has a distal end 12a, a proximal end (not shown, as it is within a portion of device 10, and a longitudinal axis (not shown), which may or may not be co-linear with the longitudinal axis 18 of device 10. Shaft 12 may optionally define one or more lumens in which one or more inner members may be disposed. These inner members may be other, smaller cross-section shafts, tensile members, rods, or tubes as required. Shaft 12 may be an assembly of one or more members and is not necessarily a single shaft. The shaft may include tubes of varying internal dimensions or external dimensions, or both.

Device 10 may include a mechanism 19 for retaining a portion of an implant 20 at a smaller dimension that the implanted or deployed dimension. Such a retaining or securement mechanism 19 (illustrated in FIG. 1 as a square) must release the portion to deliver and/or deploy the implant 20. In some embodiments, the securement and release mechanism 19 has a release member 22 (illustrated in FIG. 1 as a rectangle), which may be moved toward the extracorporeal end of device 10 a predetermined distance to release the portion of the implant. Details of examples of possible securement and release mechanisms 19 may be found in FIGS. 20-28. Release member 22 is coupled to an externally actuatable apparatus to move it toward the extracorporeal end of device 10. In some embodiments, release member 22 is secured to a tensile member 24 at a point 25 along the length of tensile member 24, which is pulled toward the extracorporeal end of device 10. Such a tensile member may be referred to as a release tensile member. In some embodiments, the externally actuatable apparatus is physically coupled to shaft 12. An embodiment of such an externally actuatable apparatus 26 is illustrated by a rectangle in FIG. 1, for ease of illustration. Subsequent figures illustrate embodiments of apparatus 26 for pulling release tensile member 24 that may be coupled to shaft 12 of a device 10.

The device 10 may include a sheath 28 at least partially disposed about an inner shaft and/or within an outer (tubular) shaft and about an implant 20. This sheath may act to maintain the implant 20 at a smaller dimension than when deployed, or it may act as a barrier or lubricious surface between the outer surface of the implant and its external surroundings. Such a sheath and implant must have relative motion along a longitudinal axis of the sheath to deliver the implant to the body. Some embodiments of a sheath may be alternatively termed an "outer member," making shaft 12 an "inner member" relative to such a sheath. In some embodiments of the device, the sheath is axially retractable. In some embodiments of the device, the implant is axially advanceable. In some embodiments, the mechanism that provides relative motion between the sheath and implant is separate from the apparatus for pulling the release tensile member. In some embodiments, the axially retractable sheath is coupled to a rotatable handle 30 that may be rotated one, or preferably more than one, turn about the longitudinal axis of the shaft 12. The rotatable handle may be rotatably coupled to the shaft 12. In some embodiments, an operator of the delivery device must use one hand to hold the shaft 12 and the other to rotate the handle about the shaft 12 to retract the sheath, thereby uncovering or exposing the implant. The operator of the delivery device may, in some embodiments, simply directly pull the sheath toward the extracorporeal end of the device to retract it from about the implant.

Figure 2:
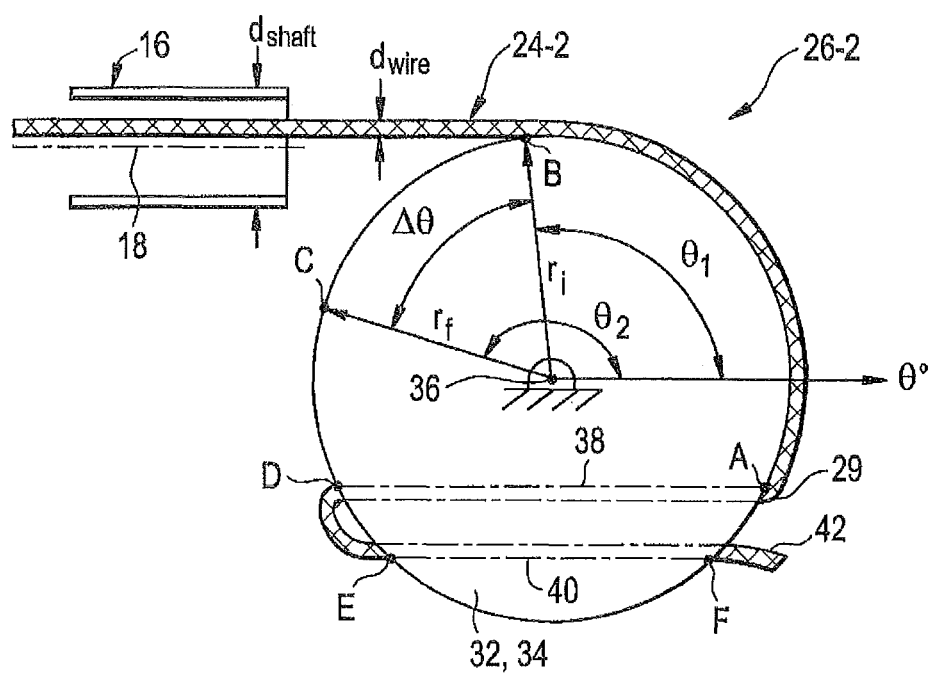
FIG. 2 illustrates a proximal portion of a medical device, a tensile member, and an embodiment of an apparatus for pulling the tensile member from the medical device.

Describing FIG. 2 in this paragraph, FIG. 2 illustrates an embodiment 26-2 of an apparatus for pulling release tensile member 24-2. Tensile member 24-2 is secured to at a first point 25 (not shown in this figure, but FIG. 1) to a first member, such as release member 20 (not shown in this figure, but in FIG. 1), and is secured at a second point 29 to a second member, which is located external to the body, and may be referred to as an "extracorporeal member." A significant portion of the length of tensile member 24 between the first point 25 and second point 29 runs through a lumen of device 10, and may run one or more inner members (e.g., shaft 12)(not shown) of device 10, as well.

In some embodiments, tensile member 24-2 for at least a length may be coaxial with the longitudinal axis 18 of device 10. In some embodiments, tensile member 24-2 may run parallel to the longitudinal axis 18 of device 10.

As illustrated in FIG. 2, extracorporeal member 32 is a rotatable cam 34. Cam 34 is rotatable about pivotal axis 36. In some embodiments, pivotal axis 36 is in a fixed position with respect to distal end 16. In some embodiments, cam 34 is coupled to shaft 12 (not shown), and pivotal axis 36 is in a fixed position with respect to the portion of shaft 12 to which cam 34 is coupled. In those embodiments where cam 34 is physically coupled to shaft 12, the number, shape, and size of parts forming the mechanical connection(s) may vary according to those parameters optimized by design choice. In FIG. 2, cam 34 has a circular side profile and two through-holes illustrated in dashed lines. Tensile member 24-2 is secured to cam 34 by being threaded from right to left through the first through-hole 38 and from left to right through the second through-hole 40. As illustrated an unattached end 42 of tensile member 24-2 extends outside of second through-hole 40. A knot in tensile member 24 may not be necessary to prevent tensile member 24 from unthreading. Variations in the threading, or in other words stitching, to secure tensile member 24 to cam 34 may include, for example, more through-holes, closer placement of the through-holes, different orientations of the through-holes, or the addition of knots. Another non-limiting variation of how tensile member 24 may be secured to cam 34 includes crimping a member with a relevant dimension larger than the hole onto the end of tensile member 24 to act similarly to a knot and prevent the member (and the end of tensile member 24) from being pulled through the through-hole.

In FIG. 2, tensile member 24-2 is constant diameter, $d_{wire}=0.010$ inch, nitinol wire without the presence of or need for a lubricious coating, because its external surface is generally smooth, with sufficiently low coefficient of friction. In FIG. 2, tensile member 24-2 is a solid tensile member of circular cross section. In some embodiments, including this constant-diameter, nitinol wire embodiment 24-2, tensile member 24 has a plateau stress which is optimally chosen to be such that the typical force of deployment (actuation) does not exceed it. If the force of deployment exceeds the plateau stress, excessive stretching can result. In this embodiment, the material selected for tensile member 24-2 is also used in its martensitic phase (superelastic state). The maximum radius of tensile member 24-2, in this embodiment, prior to kinking is approximately 5 mm.

Returning to the specifics of FIG. 2, before cam 34 rotates to pull tensile member 24-2, resulting in moving release member 20 toward extracorporeal end 16 of device 10, tensile member 24-2 is already in contact with a surface of cam 34, along arc length AB, line segment AD, and line segment EF. However, as cam 34 rotates in a clockwise direction, a length of tensile member 24-2 between first point 25 (not shown) and second point 29 will come into contact with a surface of cam 34 along the arc BC. Point B is a distance, $r_i$, from pivotal axis 36, and point C is a distance, $r_f$, from pivotal axis 36, and because cam 34 is in this embodiment is substantially cylindrical, $r_i$ and $r_f$ are each equal to the radius, r, of the cylinder. Arc length BC is calculated as $r\Delta\theta$, where $\Delta\theta$ equals the radians that cam 34 must be rotated (clockwise) to bring point C to just shy of 12 o'clock, or 90° degrees, or $\pi/2$. The length of tensile member 24-2 that will come into contact with the surface of cam 34 along arc BC equals $r\Delta\theta$. In this illustrated embodiment, apparatus 26 acts like a winch, although tensile member 24-2, as illustrated, may wind around only a portion of the circumference of cam or drum 34. If the applied force to rotate cam 34 is between the outer diameter and the pivotal axis, cam 34 will act a lever in the third class of levers, but will not provide any mechanical advantage in pulling tensile member 24-2, but will instead require at least the same force as pulling it by hand.

FIGS. 3A-3C illustrate end views of three different, substantially cylindrical cams 34. The variations are in a surface 42 of a substantially cylindrical cam 34. In FIG. 3A, surface 42 has a cross section that is parallel to pivotal axis 36. In FIG. 3B, surface 42 includes a groove 44, which as illustrated has a curved concave cross section to match tensile member 24. The grooved surface 44 is between two cylindrical surfaces of equal diameter, which is greater than all diameters of groove 44. In FIG. 3C, surface 42 is a groove 45 with a curved concave cross section having a radius larger than that of tensile member 24 and extending along the entire axial distance (length) of cam 34. For ease of illustration and discussion, through-holes illustrated in FIG. 2 are only shown in FIG. 3A, but may also be present in cam 34 of FIGS. 3B and 3C.

Figure 4:
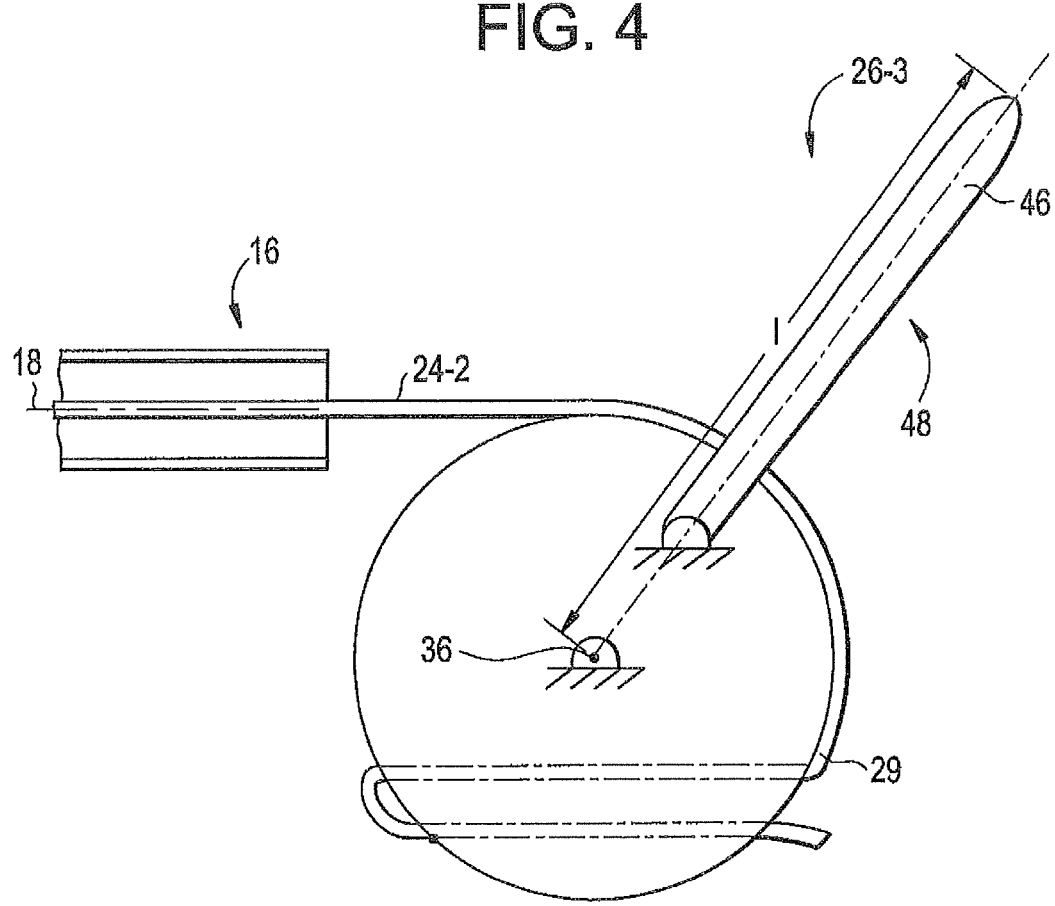
FIG. 4 illustrates a proximal portion of a medical device, a tensile member, and the embodiment of FIG. 2 for pulling the tensile member including a lever providing mechanical advantage.

FIG. 4 illustrates another embodiment of apparatus 26-3 for pulling release tensile member 24-2 that includes the components of the embodiment illustrated in FIG. 2 and adds a member 46, which in conjunction with cam 34 operates as a lever 48 about pivotal axis 36 that may provide a mechanical advantage to pulling tensile member 24-2. As illustrated, member 46 is fixedly connected to cam 34 and rotatably coupled to shaft 12. Member 46 extends in a direction away from pivotal axis 36, and its furthest point is a distance, l, from the pivotal axis, where l is greater than the radius, r, of cam 34. If the applied force is applied to member 46 at a distance from the pivotal axis greater than the distance the point at which tensile member 24-2 applies its force (tension) is from the pivotal axis, then lever 48 will operate as a lever in the second class of levers. If the applied force is applied at that distance, l, on member 46, cam 34 will pull tensile member 24-2 with a modified force that is proportional to the applied force by a factor of l/r, the maximum mechanical advantage of this embodiment.

Figure 5:
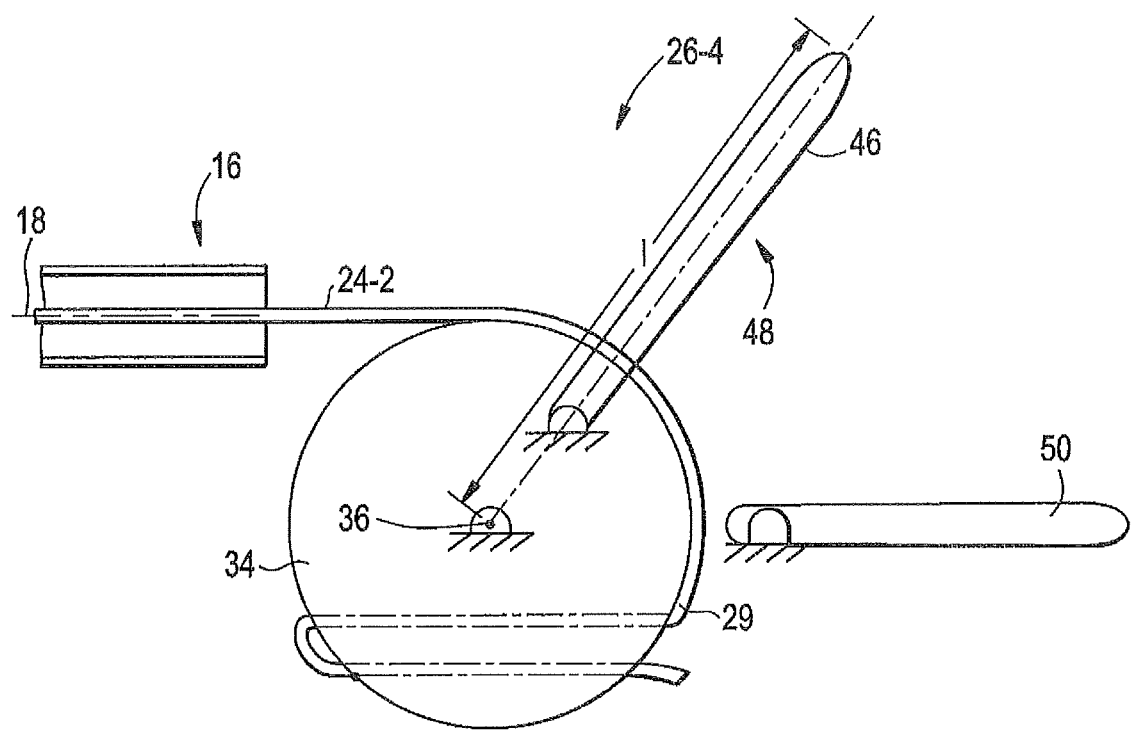
FIG. 5 illustrates the embodiment of FIG. 4 including a grip.

FIG. 5 illustrates yet another embodiment 26-4 of apparatus 26 for pulling release tensile member 24-2 that includes the illustrated components of the embodiment illustrated in FIG. 4 and adds a grip 50. Grip 50 is illustrated as independently coupled to shaft 12. One of ordinary skill in the art will recognize that structures connecting cam 34 to shaft 12 may be designed to include structures also connecting grip 50 to shaft 12. In some embodiments, grip 50 may be held in one hand and member 46 held in the other and rotated toward grip 50 to pull tensile member 24 and move release member 20 toward extracorporeal end 16 of device 10. However, in some embodiments, grip 50 and member 46 may be held in one hand, with for example a thumb in contact with member 46 and one or more fingers of the same hand in contact with grip 50. In some embodiments, grip 50 may be disposed within the range of typical distances between human thumbs and fingers in a natural cupped configuration. In some embodiments, grip 50 may have a surface contoured to match the surface of the expected digit to contact it. In some embodiments, member 46 may have a surface contoured to match the surface of the expected digit to contact it. Grip 50 is a rigid body that will receive and transmit forces from the operator in contact with it to prevent the shaft 12 from moving an unacceptable amount as a result of the forces applied to member 46 to pull tensile member 24-2, thereby moving release member 20.

In some embodiments, Grip 50 may be semi-rigidly coupled to shaft 12, such that apparatus 26 may be flexible relative to shaft 12 or to the remainder of device 10.

In some embodiments of device 10, the entire apparatus 26 may be semi-rigidly coupled to shaft 12, such that apparatus 26 may be elastically flexible relative to shaft 12, yet not buckle or significantly compress under the load applied to pull a length of tensile member 24 from device 10.

Figure 6:
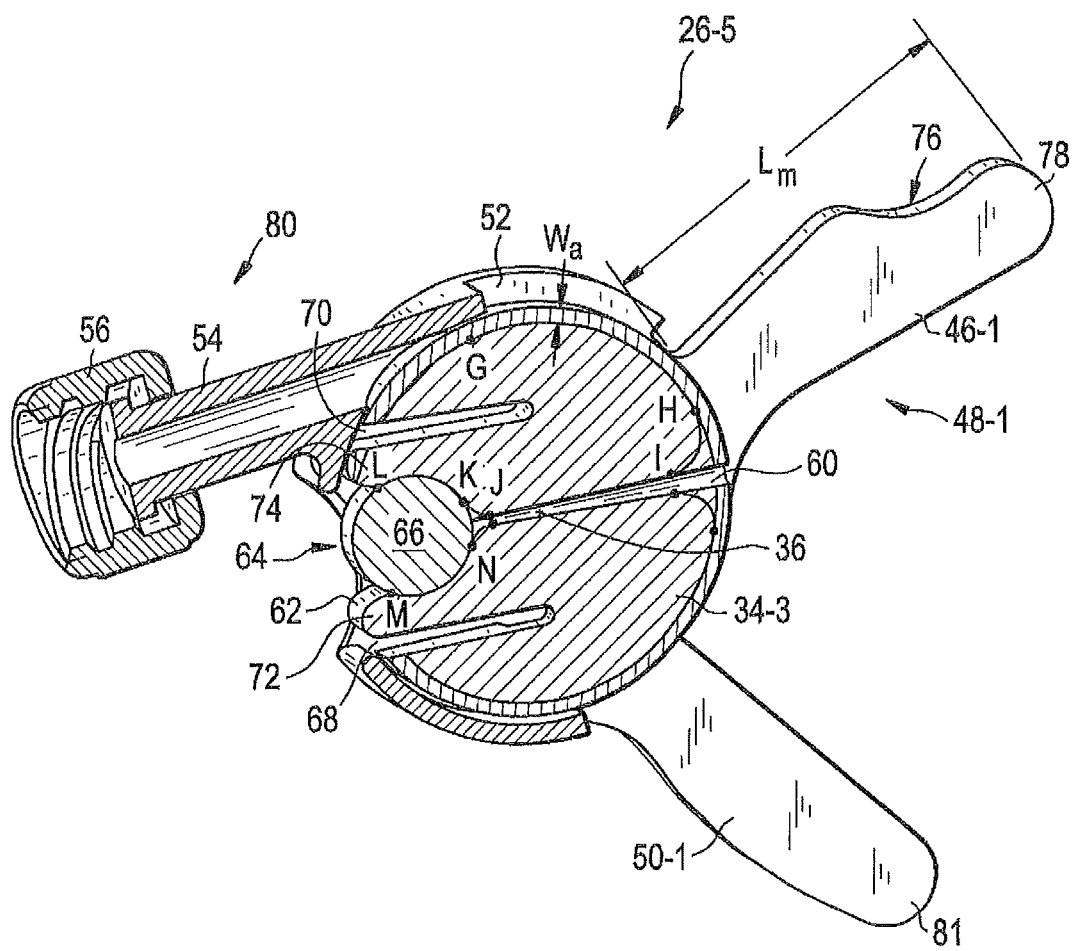
FIG. 6 illustrates a cross-sectional view of another embodiment of an apparatus for pulling the tensile member.

FIG. 6 illustrates a cross-sectional view along a centerline of a fifth embodiment 26-5 of an apparatus 26 for pulling a tensile member. The illustrated embodiment is intended for one-handed operation. For clarity, tensile member 24 and extracorporeal end 16 are not illustrated, but should be understood to be the same or similar to those illustrated in FIGS. 2, 4, and 5. For clarity, only one half of the fifth embodiment is illustrated. Unless otherwise stated, the half not illustrated mirrors the half of FIG. 6.

In FIG. 6, lever 48-1 consists of an integrally formed member 46-1 and cam 34-3. Lever 48-1 is rotatably coupled to shaft 12, and is rotatable about pivotal axis 36, which is in a fixed position with respect to the portion of shaft 12 to which lever 48-1 is coupled, and with respect to longitudinal axis 18 of device 10. Lever 48-1 is partially disposed within housing 52. Housing 52 is connected to tube 54, and tube 54 is coupled directly or indirectly to a proximal end of shaft 12 by a threaded cap 56. Tube 54 has an annular flange at its distal end captured between a distal facing annular surface of threaded cap 56 and a proximal facing surface (not shown) connected to the extracorporeal end of device 10 and removably, but fixedly held in place relative to the extracorporeal end of device 10 when the threads on the inner tubular wall of cap 56 are engaged with mating threads on extracorporeal end of shaft 12. In some variations of this embodiment, and in some embodiments of apparatus 26, the male/female ends of the thread arrangement can be reversed from what is illustrated in FIG. 6. For example, threaded cap 56 may not be included if the mating part coupled or connected to shaft 12 has female threads to receive male threads on the exterior of tube 54. As one of ordinary skill in the art of mechanical connections will recognize, there are other embodiments in which threaded cap 56 is also not necessary.

In FIG. 6, cam 34-3 is a short cylinder with a diameter, d, of about 2 cm and a height, h, of 5 mm, with an annular groove centered on the cylindrical surface of cam 34-3. Annular groove has a thickness of less than 1 mm, and a depth (annular width, $w_a$) of about 2 mm. Annular groove is defined by opposing straight side walls, less than 1 mm apart, and a cylindrical surface about 4 mm less in diameter than that of the cylinder.

In FIG. 6, the means for securing tensile member 24 to cam 34-3 includes a through-hole 60 across a diameter, where through-hole 60 has a conically shaped section with a larger diameter hole in the radially outer most cylindrical surface, which constantly tapers to the center of cam 34-3. Through-hole 60 has a first opening, which is larger than the larger diameter hole, as the edges that would have been formed by the intersection of the tapered through-hole 60 and the "bottom" or "inner" surface of the annular groove have been radiused to remove the edge. Continuing along the diameter of the cylinder toward the opposite side from the first opening, through-hole 60 has a constant diameter section matching the smallest diameter of the conical section. Through-hole 60 has a second opening in an external surface 62. This external surface 62 defines a space 64 in the short cylinder that intersects the entire cylindrical surface. Two other spaces, in the form of slots 68 and 70, one on either side of space 64, provide room for the resulting retaining arms 72 and 74 to deflect into slots 68 and 70, respectively when a cylinder 66, which is sized to fit into space 64, is pushed into space 64 and mechanically interferes with portions of arms 72 and 74. Slots 68 and 70 are generally rectangular and intersect the cylindrical surface and top and bottom circular surfaces of the short cylinder and extend parallel to the diameter along through-hole 60 and end in cylindrical surfaces at the diameter perpendicular to the diameter along the through-hole. Arms 72 and 74 "snap" back into their unstrained position, as illustrated, and surround about two hundred forty degrees (240°) of cylinder 66. A discussion of the preferred path of the tensile member and its interaction with cylinder 66 and cam 34-3 may be found in a few paragraphs below.

In FIG. 6, member 46-1 projects away from the cylindrical surface of cam 34-3 along a generally radial line for a distance, $L_m$, of about 2 cm. Member 46-1 is an elongated, plate-like structure with flat surfaces in the same plane as the top and bottom surface of short cylinder of cam 34-3. A surface 76 of member 46-1 near free end 78 has a contour to approximately match the curvature of a portion of a human thumb (not shown).

In the embodiment of FIG. 6, tensile member 24 (not illustrated) will exit the lumen of shaft 12 and immediately pass through the lumen of tube 54 until it enters annular groove of cam 34-3 and contacts the inner cylindrical surface of annular groove of cam 34-3 at a point G. Tensile member 24 then will stay in contact with the inner surface of annular groove, following the constant radius curvature for less than ninety (90) degrees along arc GH, then following a radiused edge along arc HI into through-hole 60 across the diameter of cam 34-3. Upon exiting through-hole 60 at point K, tensile member 24 wraps around cylinder 66 and returns to the second opening of through hole at point N to enter it in the opposite direction, pass through through-hole and exit it through first opening. Accordingly, tensile member 24 is between almost matching cylindrical surfaces of cylinder 66 and external surface 62 on two sides of space 64 (and of the cylinder sized to fit space 64) (arcs KL and MN) and is held by an interference fit and capstan effect.

Grip 50-1 is coupled to housing 52, and in the embodiment illustrated in FIG. 6, is a part of an integrally formed extension 80 coupled to shaft 12. Grip 50-1 projects from housing 52 away from pivotal axis 36 in a plane perpendicular to pivotal axis 36. As illustrated, grip 50-1 is an elongated, plate-like structure. One surface of grip 50-1 is curved to provide a contour between the outer cylindrical surface of housing 52 and grip 50-1 to approximately match the shape of a side of a finger of a hand of the operator.

Housing 52 is adapted to constrain lever 48' to rotate with respect to shaft 12 (and housing 52) about pivotal axis 36.

Housing 52, in FIG. 6, is a generally-cylindrically shaped structure, and its cylindrical axis is coaxial with pivotal axis 36, but it has a cylindrical cavity within it to accommodate cam 34-3 of lever 48-1. That cavity opens to the exterior to accommodate member 46-1 of lever 48-1 to be disposed in the opening and to rotate within the opening at least the desired number of degrees about pivotal axis 36 for successful operation of apparatus 26. In FIG. 6, that opening is defined by the edges of circular ends of generally cylindrically shaped structure and the adjacent portions of the cylindrical wall joining the two circular ends.

Housing 52 may have other features as desired for other functions it may perform.

In FIG. 6, housing 52 has another opening, to accommodate introducing cylinder 66 into space 64 from the exterior of housing 52.

While not illustrated in FIG. 6, depending on the material selected for housing 52 and grip 50-1, a strengthening rib projecting in a plane perpendicular to the otherwise plate-like structure 50-1 may extend from free end 81 to within a few millimeters of the cylindrical axis of housing 52.

Also not illustrated in FIG. 6, housing 52 may include a deflectable member that is designed to mechanically interfere with the rotation of lever 48-1 until a predetermined moment is applied that will deflect the deflectable member and allow lever 48-1 to rotate a predetermined number of degrees. Such a deflectable member may be a ratchet tooth to permit lever to rotate in only one direction, or it may defect in both rotational directions. Cam 34-3 may be adapted to create a recess in the circular surfaces ("top" and "bottom" of the short cylinder) sufficient to accommodate deflectable member except where such mechanical interference is desired. Alternatively or additionally, cam 34-3 may be adapted to create a projection sufficient to mechanically interfere with deflectable member only where desired.

Housing 52 may be formed from two or more parts that are assembled by fastening means for ease of inserting cam 34-3 and/or lever 48-1 into housing 52.

Figure 7:
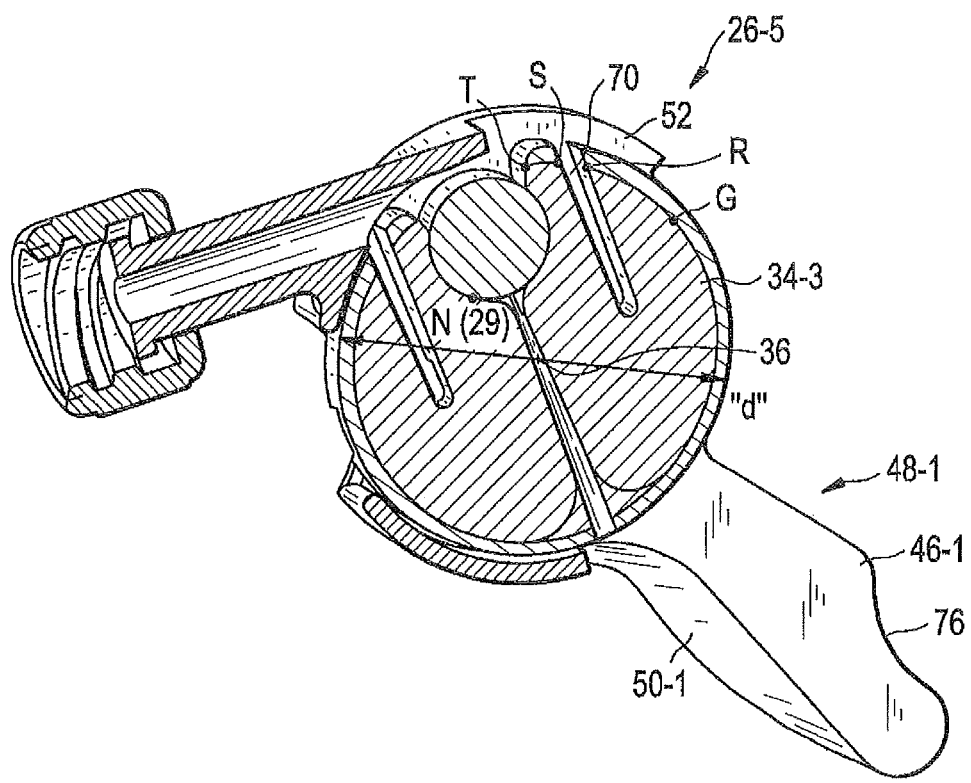
FIG. 7 illustrates a cross-sectional view of the apparatus of FIG. 6 wherein the cam and lever have been rotated with respect to the elongated shaft, thereby pulling the tensile member.

Turning to FIG. 7, which illustrates the embodiment 26-5 of apparatus 26 of FIG. 6, lever 48-1 has rotated with respect to shaft 12 through a prescribed angle and accordingly with respect to housing 52 about pivotal axis 36. Point G of cam 34-3, which had been in a position of about 90 degrees, is now illustrated in a position of about 0 degrees. Tensile member 24 (not shown) is now in contact with additional portions the inner surface of annular groove of cam 34-3 (arc GR and ST), and extends across the gap between points R and S, the gap being part of slot 70. An additional length of tensile member 24 (not shown) between first point 25 (not shown here) and second point 29 (point of tensile member 24 in contact with point N, recognizing that several other points of tensile member 24 between point H and N are also effectively secured to the extracorporeal member) is now been pulled out of device 10. In this embodiment, that length of tensile member is about ½ inch. Member 46-1 is now disposed between two parallel and mirror imaged parts of grip 50-1. The contoured surface 76 of member 46-1 designed to be in contact with a portion of a thumb is adjacent to the straight side of grip 50-1, giving a physical indication to the operator that lever 48-1 has reached its intended extent of rotation about pivotal axis 36.

Figure 8:
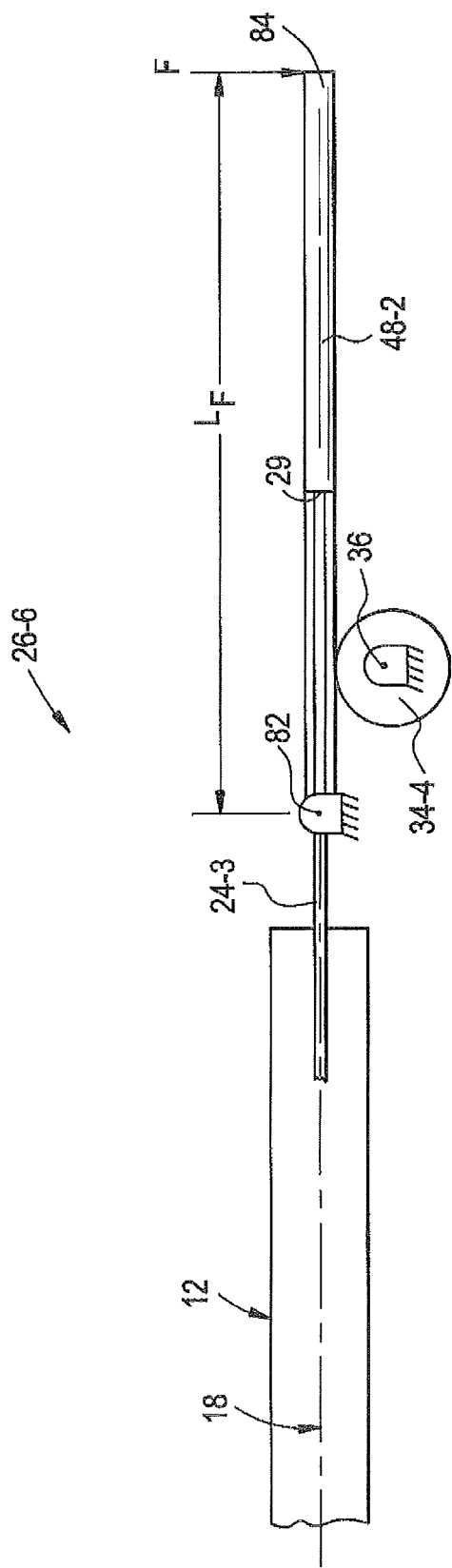
FIG. 8 illustrates a portion of an elongated shaft, a tensile member, and a third embodiment of an apparatus for pulling the tensile member.

FIG. 8 illustrates a sixth embodiment 26-6 of apparatus 26 for pulling tensile member 24. In this embodiment, lever 48-2 is rotatably coupled to shaft 12 to rotate about pivotal axis 82, and cam 34-4 is rotatably coupled to shaft 12 to rotate about pivotal axis 36. Pivotal axes 36 and 82 are parallel. Tensile member 24-3 is secured to lever 48-2 at point 28 along the length of tensile member 24-3. As illustrated, lever 48-2 is longitudinally aligned with longitudinal axis 18 of shaft 12, and tensile member 24-3 is not in contact with cam 34-4. Lever 48-2 extends along that longitudinal axis 18 beyond the point where tensile member 24-3 is secured to it, such that a force, F, applied at its free end 84, as illustrated, would have a lever arm of, LF, from pivotal axis 82. Rotatable cam 34-4 is substantially cylindrically shaped, and therefore maybe referred to as a drum or as a pulley depending on other characteristics not illustrated in FIG. 7. Cam 34-4 is positioned within the circle about pivotal axis 82 followed by point 29 of tensile member 24-3 which is secured to lever 48-2 as lever 48-2 rotates about pivotal axis 82.

Figure 9:
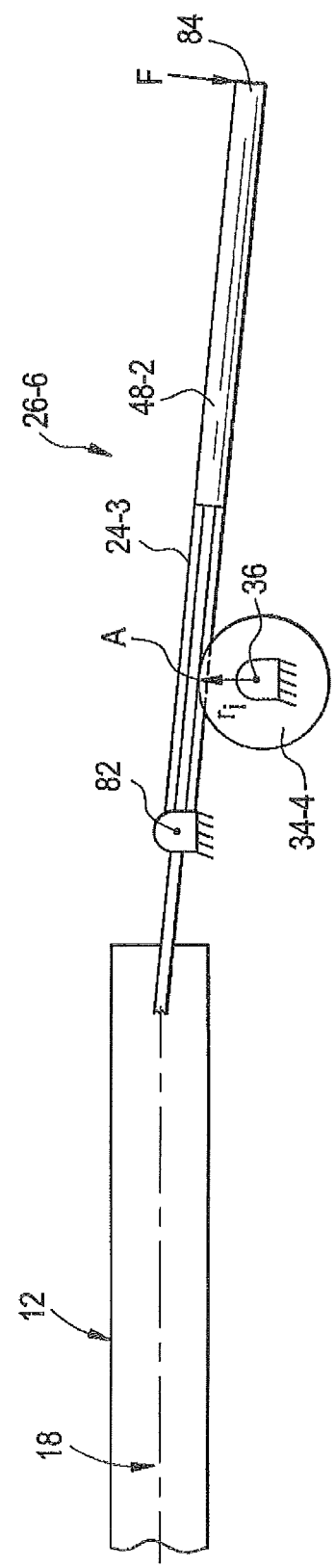
FIG. 9 illustrates the embodiment of FIG. 8 after the lever has been rotated to place the tensile member in contact with a surface of the cam.

FIG. 9 illustrates the sixth embodiment 26-5 of apparatus 26 after lever 48-2 has been rotated about pivotal axis 82 by the application of force F at free end 84 until tensile member 24-3 contacts the cylindrical surface of cam 34-4 at point A, which is at a distance, $r_i$, from pivotal axis 36.

Figure 10:
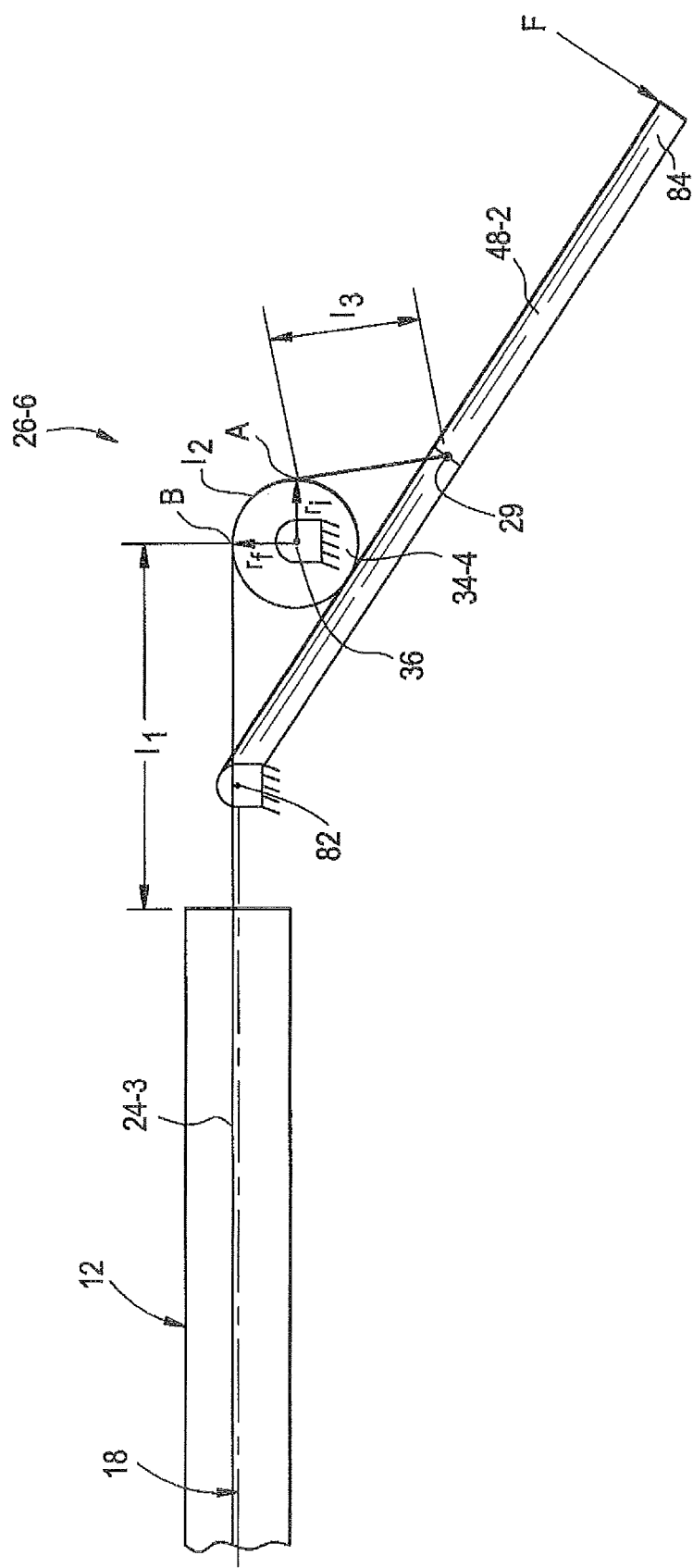
FIG. 10 illustrates the embodiment of FIG. 8 after the lever has been rotated to pull the tensile member a predetermined distance.

FIG. 10 illustrates the sixth embodiment 26-5 of apparatus 26 after lever 48-2 has been rotated approximately 45 degrees about pivotal axis 82 by the application of force F at free end 84. Tensile member 24-3 and cam 34-4 do not move relative to one another where they are in contact, which in FIG. 10 is along arc AB. Point B is a distance, $r_f$, from pivotal axis 36. As cam 34-4 has a constant radius, r, thus $r_i$ is equal to $r_f$ and all radii in between. Thus, an additional length of tensile member 24-3 has been pulled from shaft 12, which length is equal to $r(\pi*45°/180°)$. Length, $l_1$, from the plane where tensile member 24-3 exits the lumen of device 20 to the point where tensile member 24-3 contacts cam 34-4 is unchanged from FIG. 9, as is the length, $l_3$, from point A to point 29.

Figure 11:
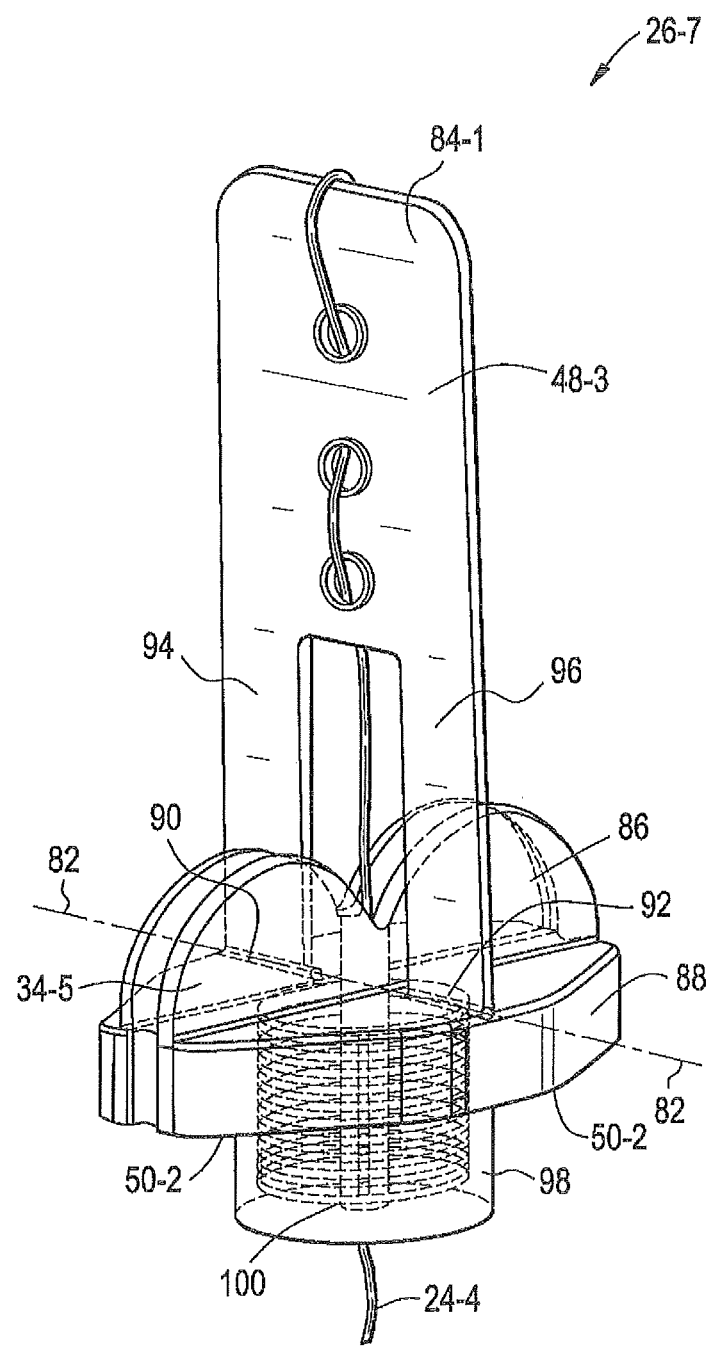
FIG. 11 illustrates another embodiment of an apparatus for pulling the tensile member.

FIG. 11 illustrates a seventh embodiment 26-7 of apparatus 26 for pulling tensile member 24. Lever 48-3 is rotatably coupled to shaft 12 (not shown) about pivotal axis 82. Tensile member 24-4 is secured to lever 48-3. The means of securing in the sixth embodiment includes three cylindrical through-holes each with a cylindrical axis intersecting, and perpendicular to, longitudinal axis 18 of shaft 12, at least in the position illustrated in FIG. 11. Tensile member 24-4 is stitched from one side of plate-like lever 48-3 to the other and back and forth through the through-holes and then loops around free end 84-1 with the end of the tensile member disposed in the through-hole nearest the free end.

The sixth embodiment includes two cams, only one of which will be selected and used in the operation of apparatus 26. Cam 34-5 is in a fixed position with respect to shaft 12 and is disposed between the arc defined by the locus of points that point 29 of tensile member 24-4 follows as lever 48-3 is rotated about pivotal axis 82 and pivotal axis 82. Cam 34-5 has a plate-like, half cylinder or disk shape, but with a groove centered on the surface of cam 34-5 between the half circle "top" and "bottom" surfaces of the half-cylinder or half-disk. The groove has a transverse cross section with a constant radius for contact with tensile member 24-4. The radius of the groove is much larger than the radius of the constant diameter tensile member 24-4 illustrated in FIG. 11.

In FIG. 11, cam 86 having a mirror image structure of cam 34-5 is integrally attached to cam 34-5, and also disposed in a fixed position with respect to shaft 12. In this embodiment, an operator of apparatus 26 may operate it as easily with the left hand as the right hand, due to the presence of cam 86 and cam 34-5. If lever 48-3 is rotated in one direction about pivotal axis 82, one of cam 34-5 and cam 86 comes into contact with tensile member 24-4 and the other does not. If lever 48-3 is rotated in a second direction, opposite to the first direction, the other cam comes into contact with tensile member 24-4 to the exclusion of the remaining cam.

As illustrated in FIG. 11, cams 34-5 and 86 are both mounted to a base 88, which incorporates a grip 50-2 for one or more fingers of the same hand as the thumb that is intended to apply the force to rotate lever 48-3 about pivotal axis 82. Lever 48-3 is rotatably connected to base 88 through two living hinges 90 and 92. Hinge 90 connects leg 94 of lever 48 to base 88 and hinge 92 connects leg 96 to base 88.

As illustrated in FIG. 11, base 88 is connected to a tube 98 which has threads on the inner diameter. The threads of tube 98 may removably secure base 88 and apparatus 26 to shaft 12, or some other component fixedly coupled to shaft 12. The lumen of tube 98 is in limited fluid communication with hole 100 between cams 34-5 and 86, and tensile member 24-4 passes through both the lumen of tube 98, an intervening gasket (not shown) to limit fluid leaking from the lumen of tube 98 and hole 100 before extending from the opening of hole 100 and passing in the space between leg 94 and leg 96 of lever 48-3 until it contacts an edge between one side of plate-like lever 48-3 and a narrow rectangular surface along the thickness of lever 48-3 between the joined ends of leg 94 and leg 96 of lever 48-3 to the main body 102. From that point, tensile member 24-4 begins the path through the three through-holes previously described three paragraphs above.

During the operation of the embodiment of FIG. 11, lever 48-3 rotates about pivotal axis 82, and tensile member 24-4 contacts cam 34-5 (or cam 86, depending on the direction of the rotation). Once in contact with cam 34-5, tensile member 24-4 slides on the surface of cam 34-5 in which it is in contact.

Figure 12:
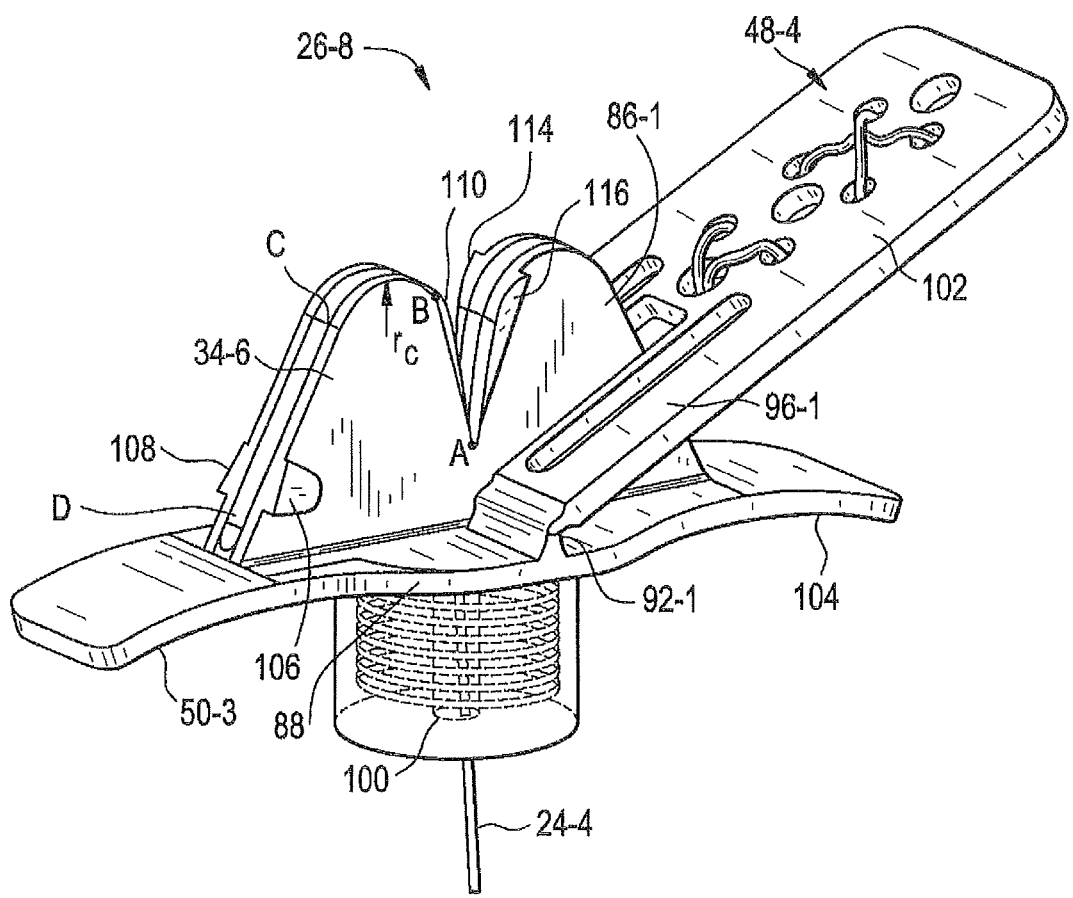
FIG. 12 illustrates yet another embodiment of an apparatus for pulling the tensile member.

FIG. 12 illustrates a eighth embodiment 26-8 of apparatus 26 for pulling tensile member. The eighth embodiment is similar to the seventh embodiment, with the following differences. Lever 48-4 has eight additional through-holes from one side of the plate-like structure to the other, six of which are cylindrical, but smaller in diameter than the three present in lever 48-4 of the sixth embodiment, and two of which are elongated. The six smaller cylindrical holes are disposed symmetrically about the longitudinal axis of lever 48-4, three on one side of the axis and three on the other. Each of the two elongated through-holes is located mostly in a respective leg of lever 48-4, and partially extends into main body 102 of lever 48-4. Base 88 is thinner and has two grips, 50-3 and 104, which extend in opposite directions from base. Grips 50-3 and 104 are each contoured to match the profile of the intended digit (finger) to contact grip 50-3 or grip 104 and apply stabilizing forces during the application of force to lever 48-4 by the thumb or other part of the same hand. Base includes two projections from the plate-like structure toward lever 48-4, each of which that narrows until it becomes the reduced section part, living hinge 90 or 92. Lever 48-4 has a mirror image of that projection on the other side of living hinge 90 or 92. Cam 34-6 and cam 86-1 have a different shape than their shape in the seventh embodiment, resulting in a different function of length of tensile member pulled from shaft 12 resulting from an input change in angle of rotation of lever 48-4. Because cam 34-6 and cam 86-1 are still mirror images of one another in this embodiment, only cam 34-6 will be described. Cam 34-6 in FIG. 12 has a straight section, segment AB, disposed at an angle to the longitudinal axis of hole 100 of about 20 degrees, which is immediately adjacent to a curved section of constant radius, $r_c$, arc BC, which is immediately adjacent to a second straight section, segment CD. The curved section, arc BC, is further away from the opening of hole 100 in a direction parallel to the longitudinal axis of hole 100. The radius, $r_c$, of arc BC is smaller than the radius of cam 34-6 from the seventh embodiment. Cam 34-6, as illustrated in FIG. 12, includes four ratchet teeth 106, 108, 110, and 112 (not easily visible on cam 34-6, but a mirror image ratchet tooth 114 is visible on cam 86-1). Ratchet teeth 106 and 108 are mirror images of each other if the mirror is placed on the bisecting plane of the groove of cam 34-6, as are ratchet teach 110 and 112. Ratchet teeth mechanically interfere with lever 48-4 and due to their wedge-like design, gradually increase that interference as lever 48-4 is forced to rotate past them. In this embodiment, cam 34-5 will not deflect to permit relative motion of lever 48-4 and cam 34-5, but the thin portion of each of leg 94 and leg 96 will deflect toward the respective elongated through-hole until the lever has moved past the ratchet teeth. At that point the thin portion will return to its undeformed position as illustrated in this figure, until lever 48-4 rotates to place it against ratchet teach 106 and 108, near the end of the intended rotation. As illustrated, lever 48-4 has been forced past ratchet teeth 114 and 116 of cam 86-1, and is approaching interference with ratchet teeth 118 and 120 (shown in FIG. 13), which are mirror images of ratchet teeth 106 and 108, if the mirror is placed between cam 34-6 and cam 86-1 on the bisecting plane of lever 48-4. The inclusion of ratchet teeth (as compared with a member deflectable in either direction of rotation) is that an operator has a visible indicator that tensile member 24-4 has been pulled, at least part way. It may be desirable not to use the device to which apparatus 26 is coupled if such pulling was accidental rather than intended. A last difference between the seventh and eighth embodiment of apparatus is that in the eighth embodiment, a subset of the cylindrical through-holes are used in the means to secure tensile member 24-4 to lever 48-4, and the stitching pattern has changed.

Figure 13:
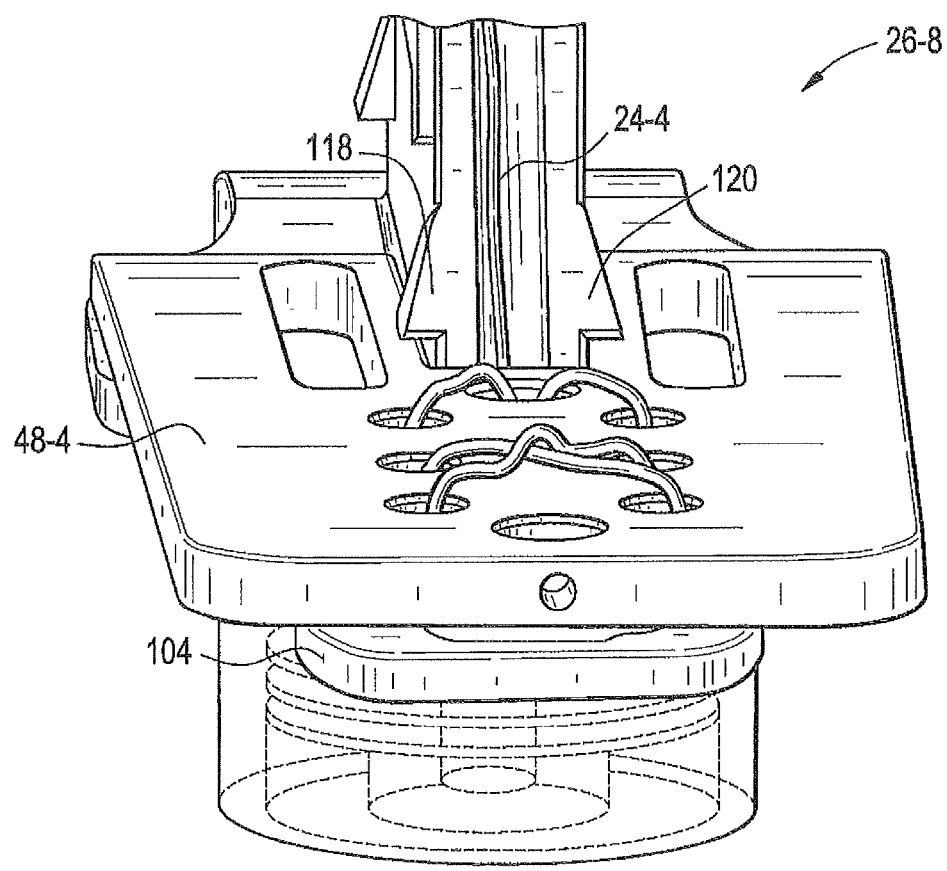
FIG. 13 illustrates the embodiment of FIG. 12 after the lever has been rotated past a ratchet tooth.

FIG. 13 illustrates a partial view of the eighth embodiment 26-8 of apparatus 26 from a different view point and after lever 48-4 has been rotated through its intended angle, past ratchet teeth 118 and 120.

Figure 14:
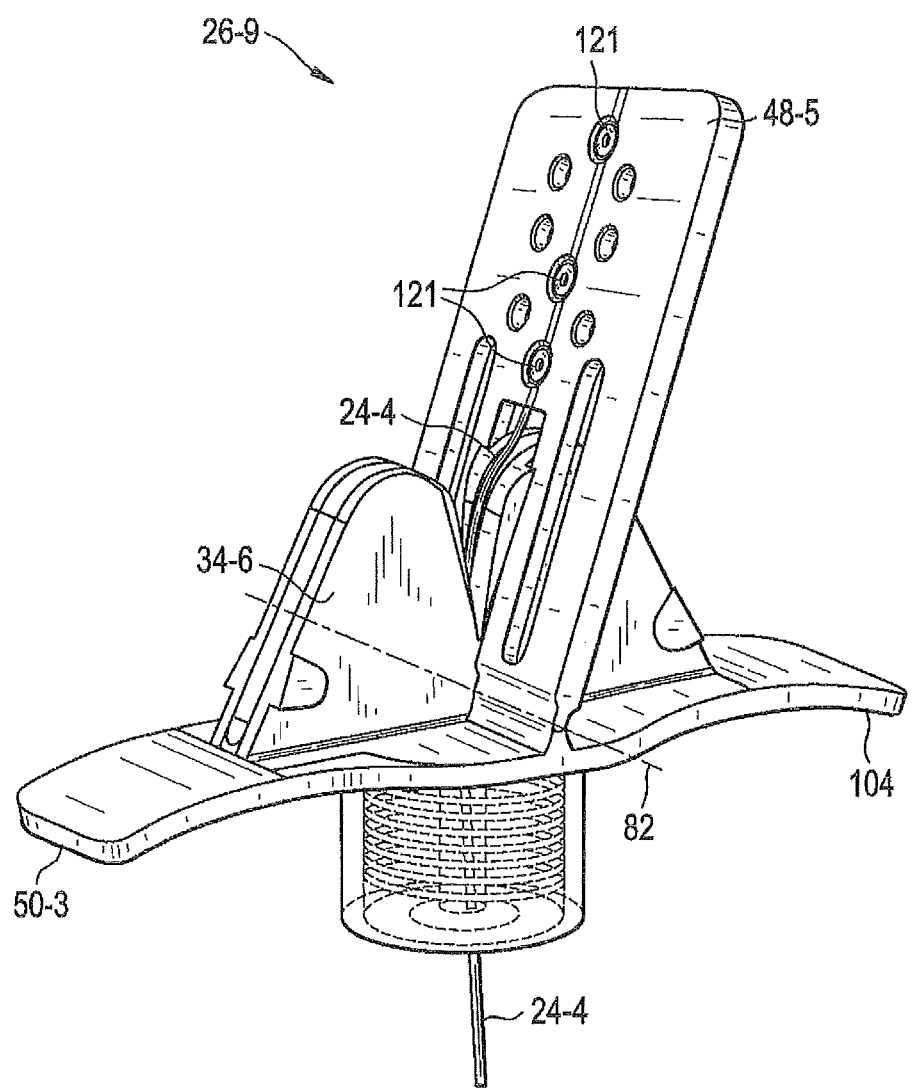
FIG. 14 illustrates the embodiment of FIG. 12 except that the means for securing the tensile member to the lever is different.

FIG. 14 illustrates a ninth embodiment 26-9 of apparatus 26 for pulling tensile member. The ninth embodiment is similar to the eighth embodiment with the following differences. Lever 48-5 has an additional through-hole along a bisecting plane of lever 48-5 with an opening on either side of main body 102 of lever 48-5 and intersecting and perpendicular to each of the three larger diameter cylindrical through-holes in lever 48-5. Tensile member 24-4, rather than being stitched through subset of cylindrical through-holes, is threaded through this additional through-hole, and secured to lever 48-5 by the addition of one or more of the three crimping disks 121 disposed in a respective one of the three larger-diameter through-holes.

Figure 15:
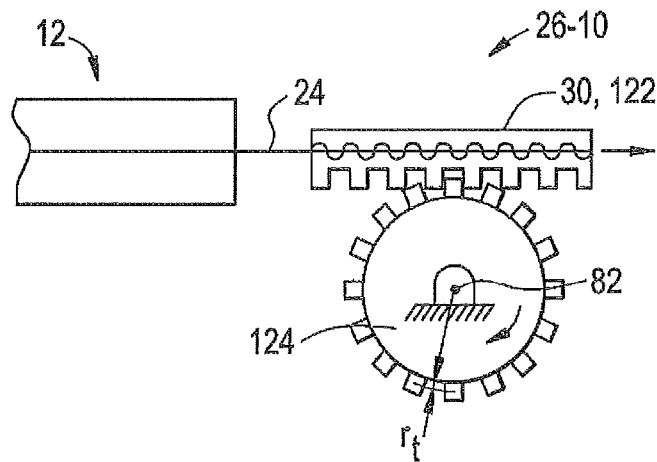
FIG. 15 illustrates another embodiment of an apparatus for pulling the tensile member.

FIG. 15 illustrates a tenth embodiment 26-10 of apparatus 26 for pulling tensile member. In FIG. 15, tensile member 24 is secured to an extracorporeal member 30, which in this embodiment is a translatable rack 122. Rack 122 cooperates with a toothed gear, a pinion 124, which is rotatably coupled to shaft 12. Rotation of pinion 124 about pivotal axis 82 moves rack a proportional distance, l, which is equal to the average radius of the teeth, $r_t$, multiplied by the change in angular position of pinion 124, delta theta, or $r_t \Delta\theta$. To pull tensile member 24, pinion 124 must be rotated in the direction illustrated by the arrow on pinion 124, which will result in the translation of rack 122 in the direction illustrated to the right of rack 122. Pinion 124 may act as a lever; however, it will not provide any mechanical advantage to the operator. If mechanical advantage is desired, a member 46 providing a lever arm having a greater radius than $r_t$ may be fixedly coupled to pinion 124, in a manner similar to the addition of member 46 to the embodiment illustrated in FIG. 4. Alternative structures to provide mechanical advantage in an embodiment of apparatus 26 such as the one illustrated in FIG. 15, include a worm gear drive, where 122 is now a rotating worm gear, which when turned, rotates the pinion (now helical) gear 124 to which the end of release tensile member 24 is fastened.

Figure 16:
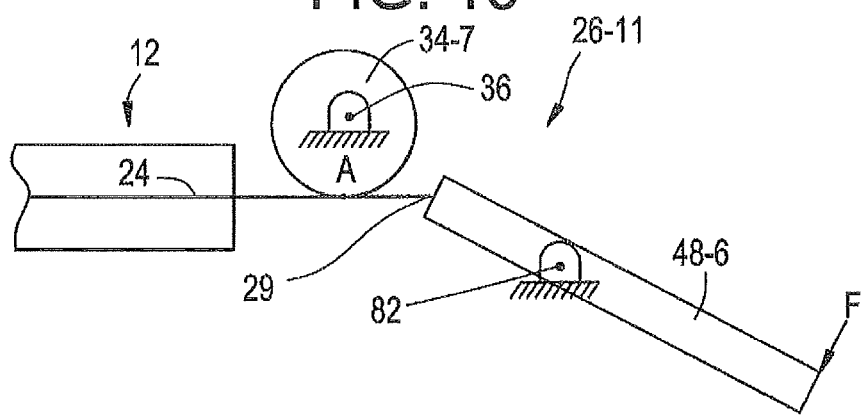
FIG. 16 illustrates yet another embodiment of an apparatus for pulling the tensile member.

FIG. 16 illustrates an eleventh embodiment 26-11 of apparatus 26 for pulling tensile member. Lever 48-6 is rotatably coupled to shaft 12, and may be rotated with respect to shaft 12 about pivotal axis 82. Tensile member 24 is rotatably secured to lever 48-6 at point 29 along its length. Cam 34-7 is a cylinder that is rotatably coupled to shaft 12 to rotate with respect to shaft 12 about pivotal axis 36. Pivotal axis and the cylindrical axis 126 of cam 34-7 are coaxial. The cylindrical surface of cam 34-7 is tangential to and in contact with tensile member 24 at point A.

Figure 17:
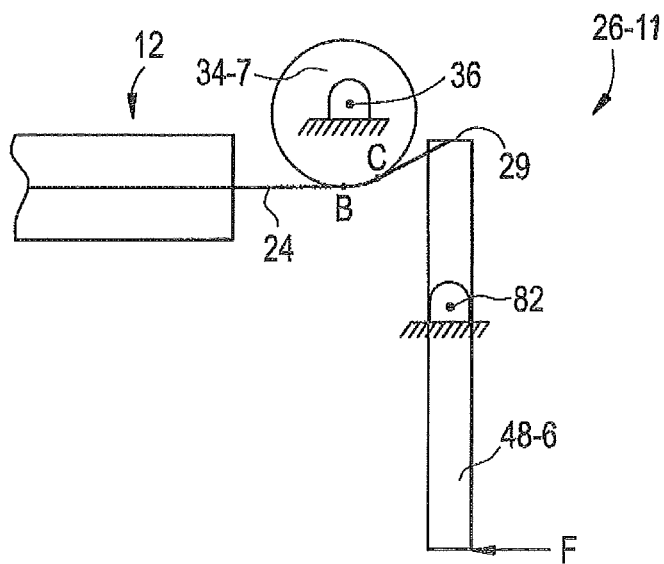
FIG. 17 illustrates the embodiment of FIG. 16 after the lever has been rotated, pulling the tensile member a predetermined distance.

FIG. 17 illustrates the eleventh embodiment after lever 48-6 has been rotated about 60 degrees about pivotal axis 82. Point 29 of tensile member 24 has followed the path indicated in FIG. 17, but has not moved from the longitudinal axis 18 of shaft 12 due to the presence of cam 34-7. Tensile member 24 increased its length in contact with cam 34-7 to a maximum of arc BC. If there is sufficient friction between tensile member 24 and the cylindrical surface of cam 34-7, then there is no relative motion between tensile member 24 and cam 34-7 where they are in contact, and cam 34-7 rotates with the advancement of tensile member 24 from shaft 12.

Figure 18:
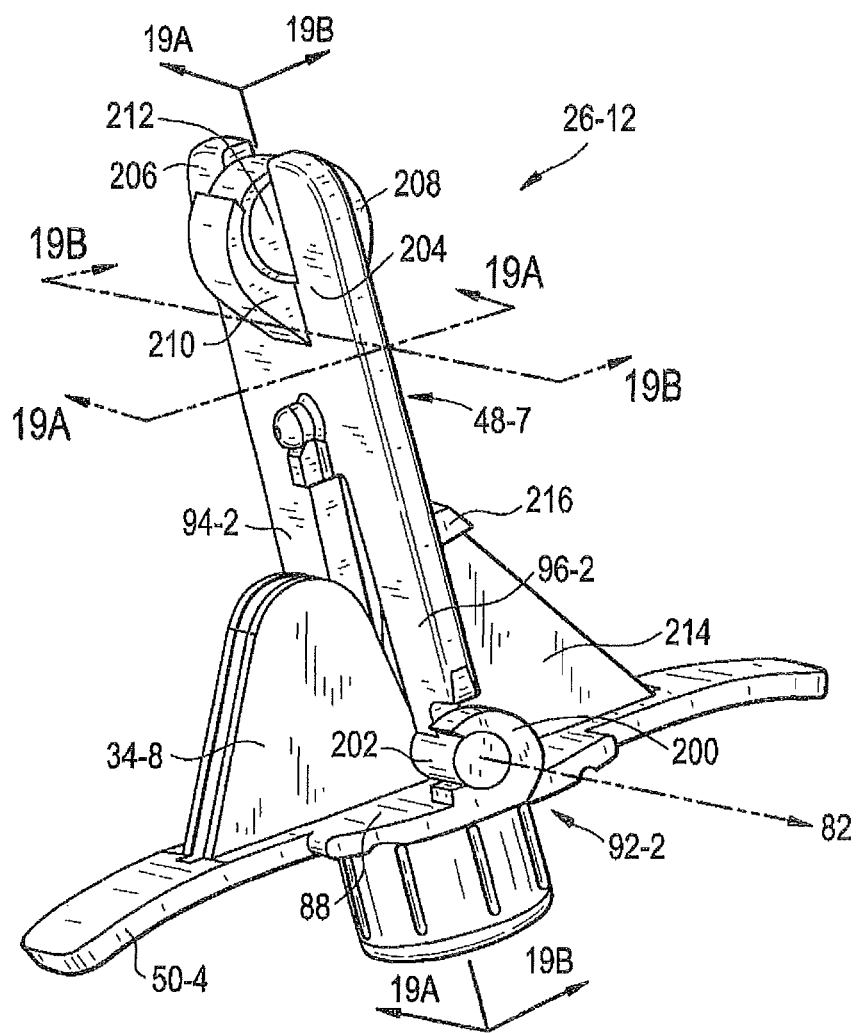
FIG. 18 illustrates yet another embodiment of an apparatus for pulling the tensile member.

FIG. 18 illustrates a twelfth embodiment 26-12 of an apparatus 26 for pulling a tensile member. The twelfth embodiment 26-12 is similar to the eighth embodiment 26-8, illustrated in FIGS. 12 and 13, however, embodiment 26-12 only has one cam 34-8, which does not have any ratchet teeth projecting from it. Hinge 92-2 is not a living hinge, but a two part hinge that snaps together for easy assembly. Hinge 92-2 includes housing 200 which encompasses a sufficient portion of the circumference of shaft 202 to hold it in place after shaft 202 has been forced into housing 200 and deflected the opening wider until it passes through the opening and the free end of housing 202 snaps back around shaft 202. Shaft 202 is integrally molded with lever 48-7. Lever 48-7 has two legs 96-2 and 94-2, but they do not have through-hole slots in them like the ninth embodiment. Lever 48-7 includes different features which contribute to the means to secure tensile member 24 to lever 48-7. The means to secure includes arm 204 and arm 206 on the right and left of front projection 210 and back projection 208. Front and back projections 210 and 208 cooperate to receive a short cylinder 212, around the partial circumference of which tensile member 24 (not shown) may be wrapped, similar to the means to secure described with regard to the fifth embodiment 36-5 illustrated in FIGS. 6 and 7. Replacing cam 86-1 is lever stop mounting 214, which projects in a normal direction away from the "top" surface of base 88. Lever stop mounting 214 provides the support for lever stop 216, which mechanically interferes with legs 94-2 and 96-2 if lever 48-7 starts to rotate away from cam 34-8 from the initial position of lever 48-7 as illustrated.

Figure 19A:
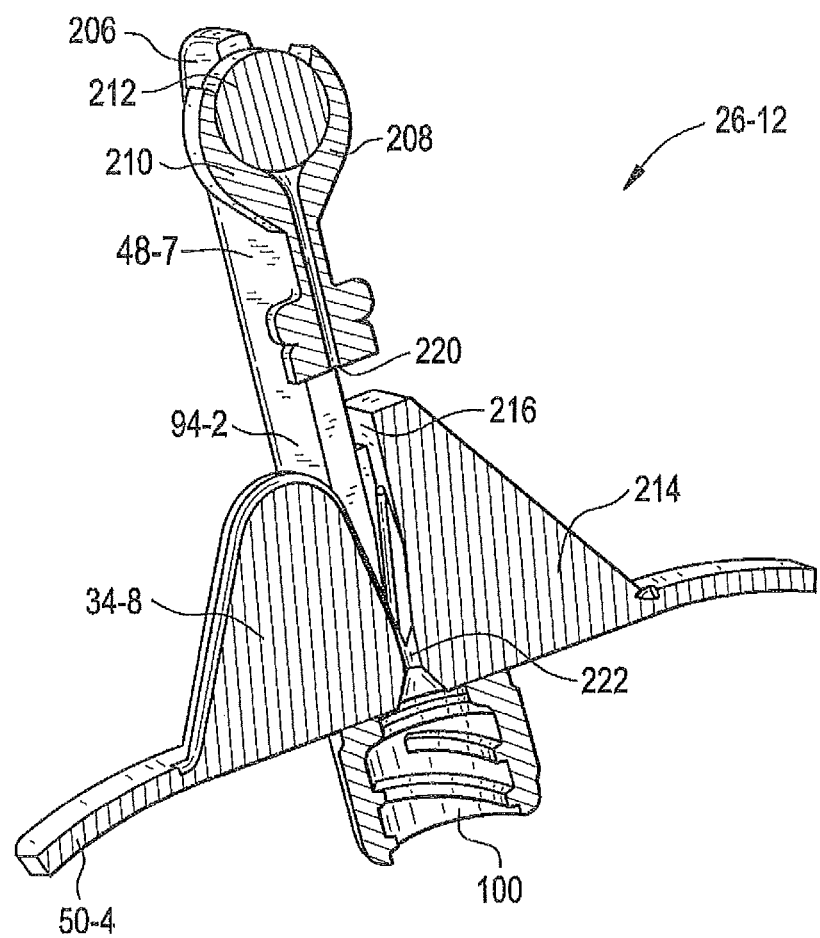
FIG. 19A illustrates a cross-sectional view of the embodiment of FIG. 18 along lines 19A-19A of FIG. 18.

FIG. 19A illustrates a cross-sectional view along line 19A-19A of FIG. 18. As illustrated, lever 48-7 defines a through-hole 220 along its longitudinal central axis through which tensile member 24 (not shown) would be threaded before wrapping clockwise or counterclockwise partially around the cylindrical perimeter of short cylinder 212 and re-entering through-hole 220 the way it exited. Lever stop mounting 214, cam 34-8, and base 88 are integrally formed and define a through-hole 222 in communication with through-hole 100. Tensile member 24 (not shown) runs from alongside shaft 12 or through a lumen in device 10 through a gasket (not shown) between the interface of hole 100 and through-hole 222, which keeps blood from significantly leaking along tensile member 24. In operation, a medical professional will apply a force to one or more of the arms 204 and 206 and back projection 208 with a digit, preferably a thumb, and rotate lever 48-7 about hinge 92 (about pivotal axis 82) to pull tensile member 24 across cam 34-8 and toward the distal end of device 10.

Figure 19B:
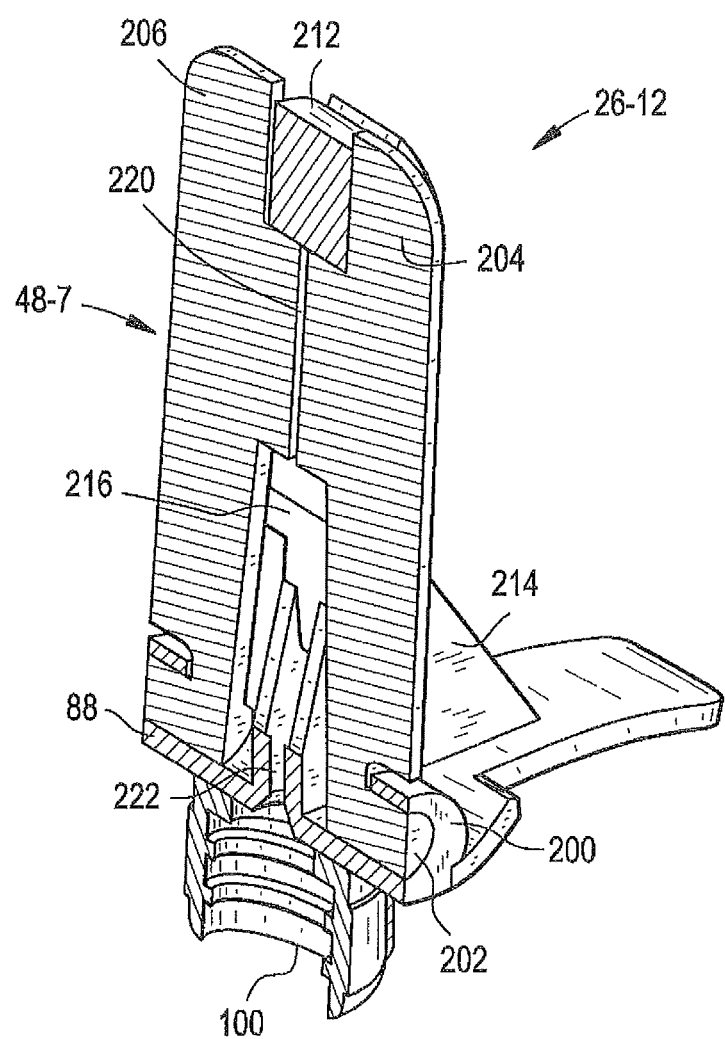
FIG. 19B illustrates another cross-sectional view of the embodiment of FIG. 18 along lines 19B-19B of FIG. 18.

FIG. 19B illustrates another cross-sectional view of FIG. 18 along line 19B-19B. Through holes 220 and 222 are visible, as are features of lever stop mounting 214, integrally formed with base 88. The interface between shaft 202 and housing 200 to form hinge 92-2 (not labeled in this figure) is also illustrated.

Figure 20:
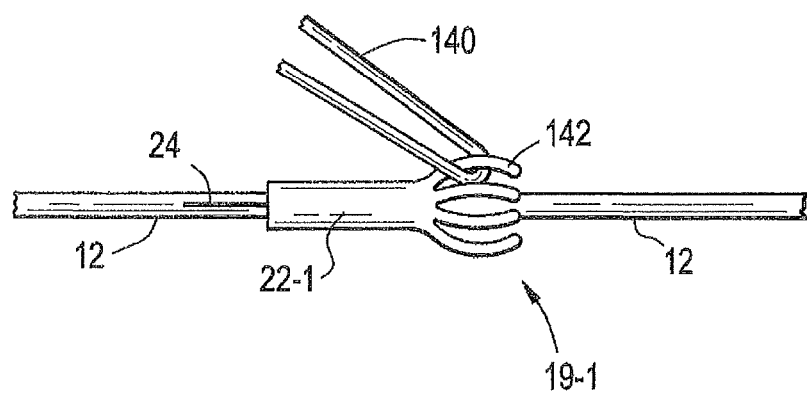
FIG. 20 illustrates a first embodiment of a securement and release mechanism to which a tensile member may be attached.

FIG. 20 illustrates a simplified embodiment 19-1 of retaining mechanism 19 for securing a portion of implant 20 to shaft 12. As illustrated tensile member 24 is attached to release mechanism 22-1 of retaining mechanism 19-1, and release mechanism 19-1 is slidably disposed about shaft 12, and may be coaxially mounted on shaft 12. Retaining mechanism 19-1 includes prongs or projections 142 that extend both distally and radially from release mechanism 22-1 and engage apex 140 of implant 20 and act to mechanically interfere with the proximal or outward radial movement of apex or hoop 140 of implant 20. When apparatus 26 is operated by a medical professional, tensile member 24 is pulled proximally and moves release mechanism 19-1 until 140 is no longer restrained by, or in other words disengages from, a prong and may expand on its own or by an expandable member. Greater detail on a retaining mechanism and associated stent interface may be found in FIG. 16 of U.S. Pat. Pub. No. 2009/0270967 and paragraphs [0091]-[0092] therein, which are explicitly incorporated herein for whatever use may be permitted.

Figure 21:
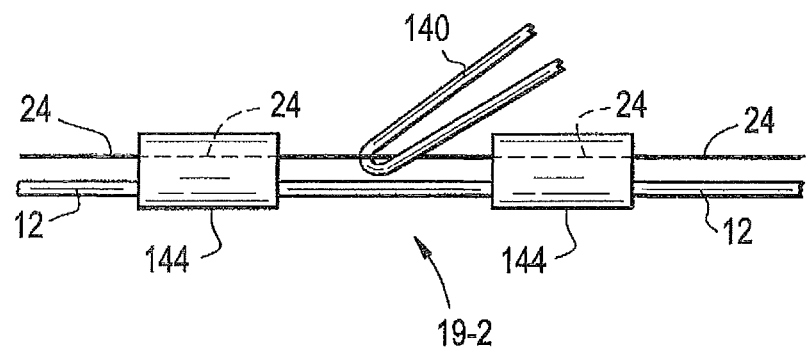
FIG. 21 illustrates a second securement and release mechanism to which a tensile member may be attached.

FIG. 21 illustrates another simplified embodiment 19-2 of a retaining mechanism 19 for securing a portion of implant 20 to shaft 12. Retaining mechanism 19-2 includes multiple wires to restrain the desired portion of the implant 20, only one of which is illustrated. In this embodiment, two collars 144 are positioned coaxially around the inner member or shaft 12 on either side of the portion of implant 20 desired to be retained at the reduced dimension, in this case, apex 140. Tensile member 24 runs through both collars 144 and apex 140 and is releasably fastened to the distal-most collar 144. Collars 144 are fixed to shaft 12 to prevent their axial motion and undesired axial motion of the implant during delivery, expansion, and deployment. Tensile member 24 may unfasten from distal-most collar 144 upon application of force from apparatus 26 and be pulled in the direction of the arrow by apparatus 26 until it clears apex 140 and permits implant 20 to expand on its own or be expanded by an expandable member.

Figure 22:
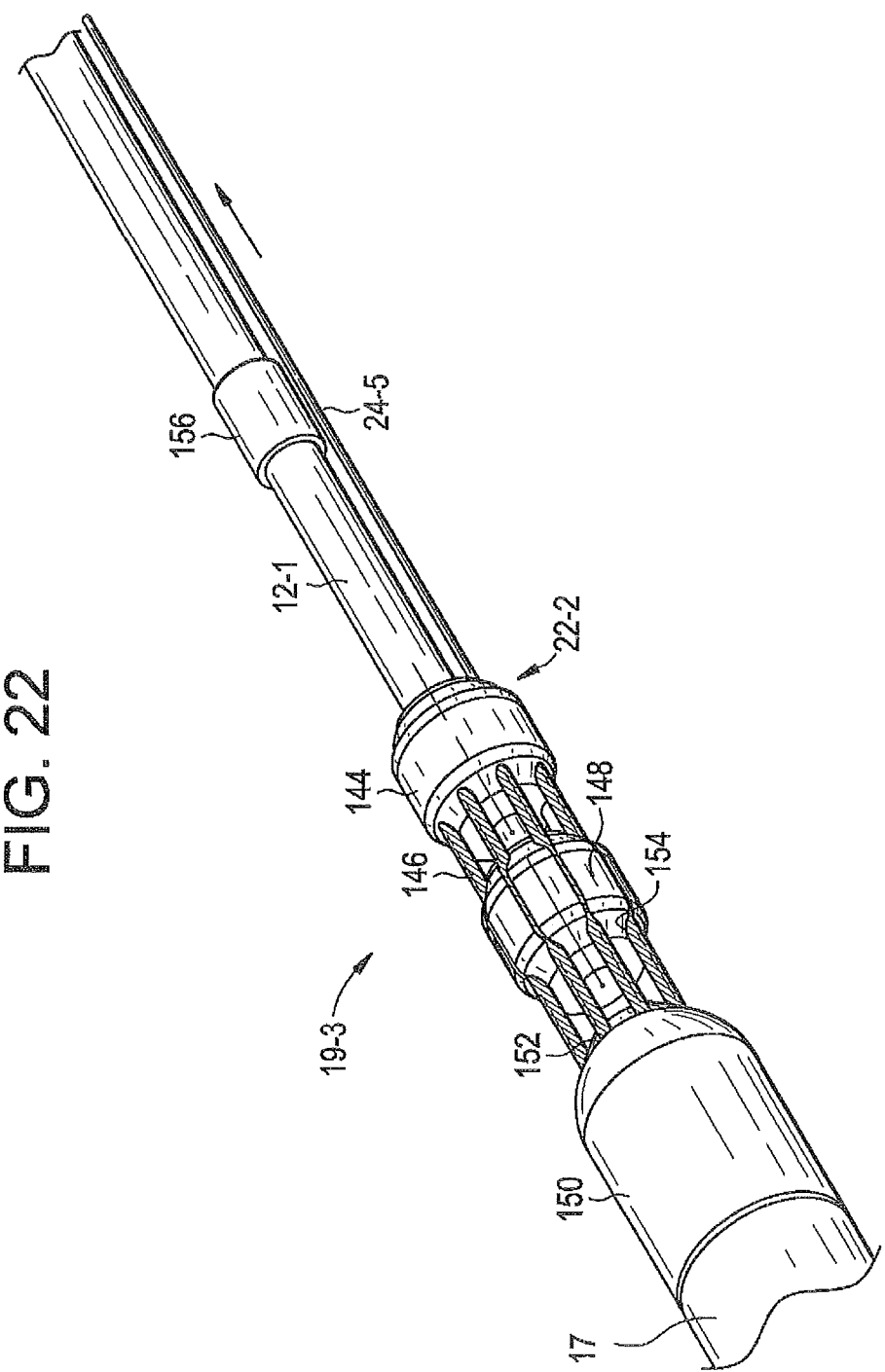
FIG. 22 illustrates a third securement and release mechanism to which a tensile member may be attached.

FIG. 22 illustrates a third embodiment 19-3 of a retaining mechanism 19. In the illustrated embodiment, retaining mechanism 19 includes four basic components: a wire holder 144, engagement wires 146, a wire guide 148, and a receiver 150 having longitudinally oriented holes 152 in which ends of engagement wire 146 are removably positioned. Wire guide 148 is fixedly mounted on shaft 12-1 and has longitudinally oriented through-holes 154 through which engagement wires 146 are slidably disposed. Wire holder 144 is slidably engaged with shaft 12-1 and engagement wires 146 are fixedly attached to wire holder 144. Tensile member 24 is secured to wire holder 144 and is disposed parallel to shaft 12.

Figure 23:
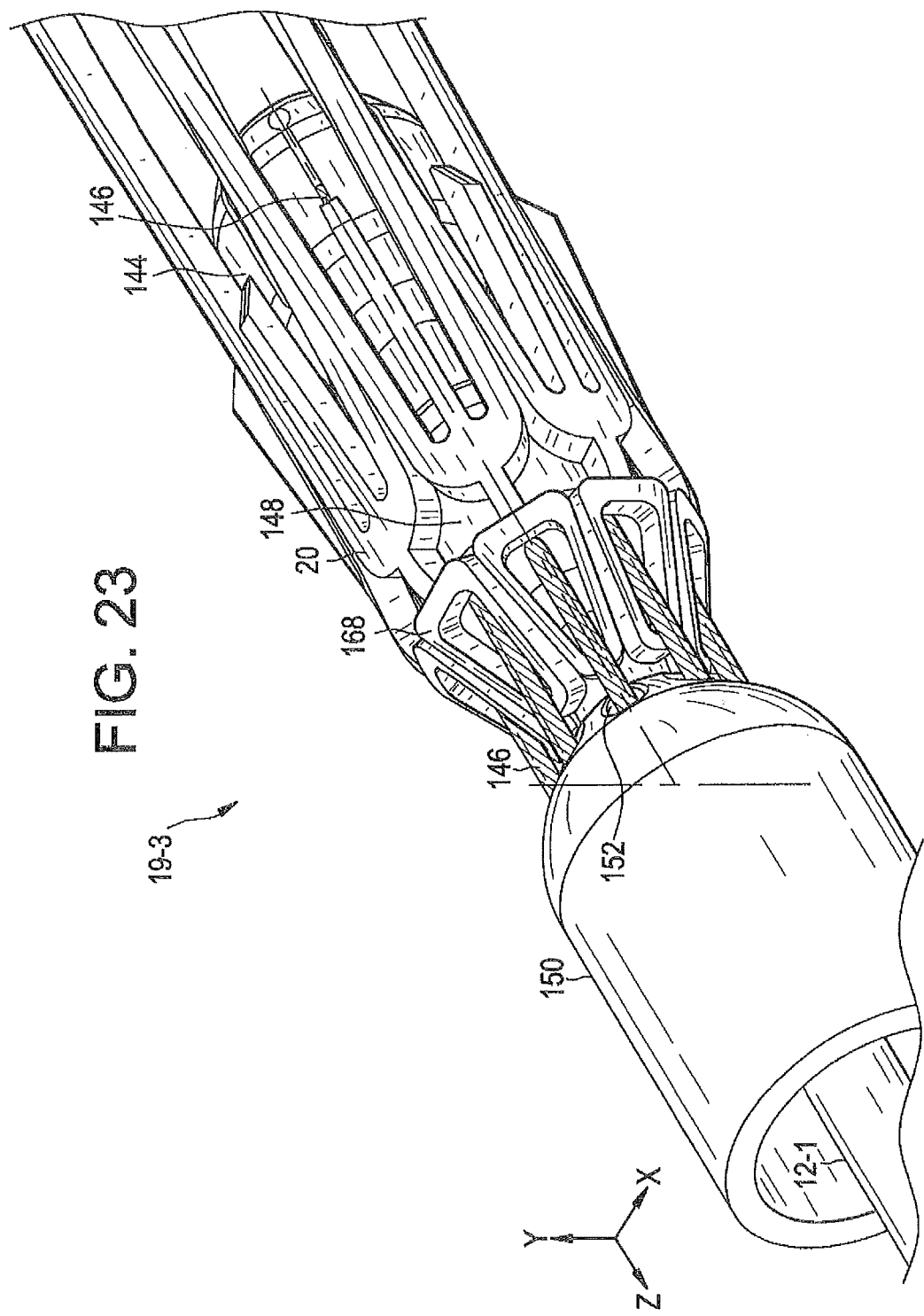
FIG. 23 illustrates the third securement and release mechanism securing the cranial end of an implant to an inner member of a delivery device.

FIG. 23 illustrates a portion of an implant 20 secured to shaft 12-1 with retaining mechanism 19-3 of FIG. 22. As illustrated, a portion of implant 20 is held in a predetermined radial position by engagement of loops 802 with engagement wires 146. Each engagement wire 146 passes under the implant 20 and through an eyelet 158 until it terminates in receiver 150.

Figure 24:
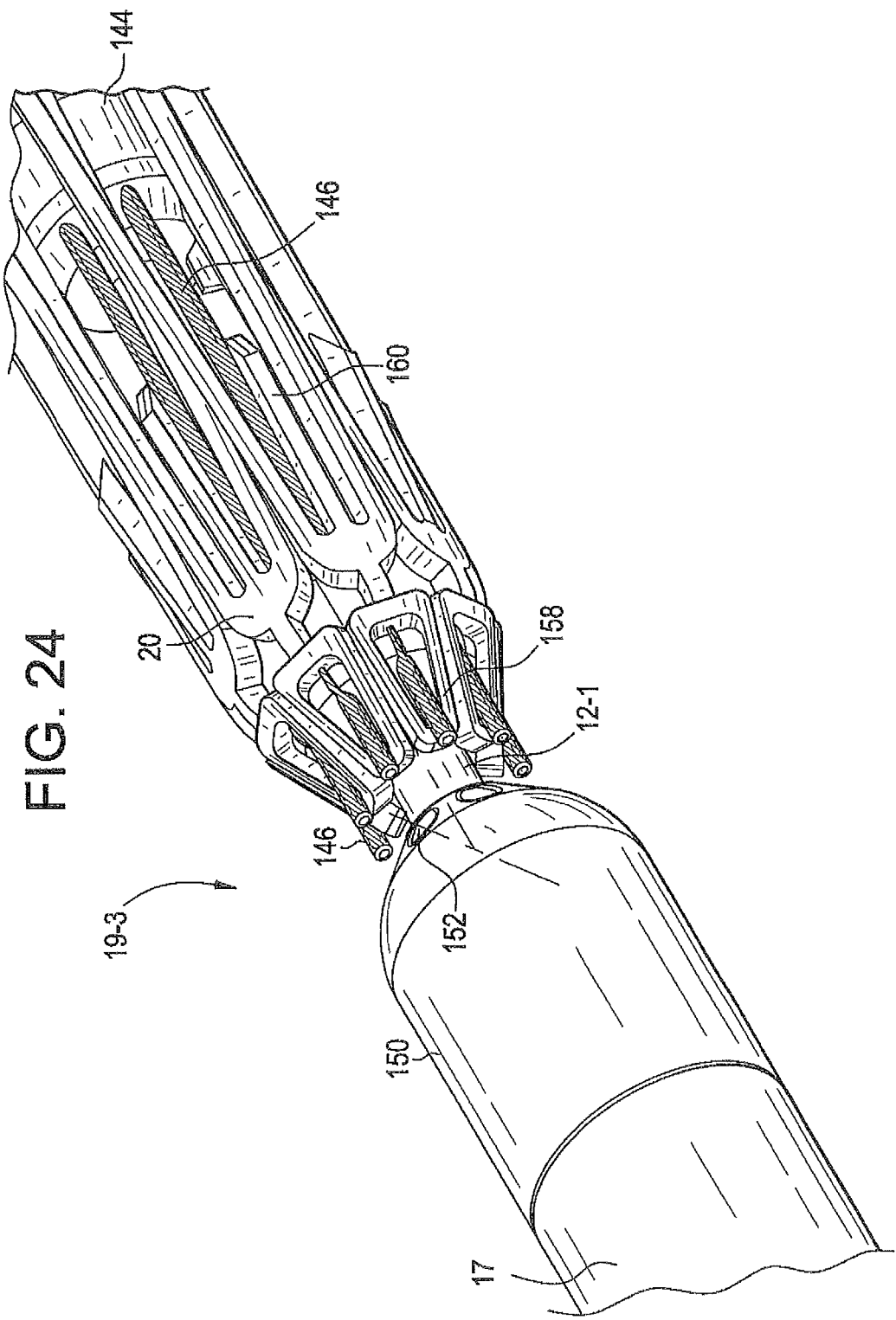
FIG. 24 illustrates the third securement and release mechanism securing the cranial end of an implant to an inner member of a delivery device, but being moved toward the extracorporeal end of the delivery device as a result of the tensile member being pulled.

FIG. 24 illustrates the embodiment 19-3 of FIG. 23 after a medical professional has begun to operate apparatus 26 to pull tensile member 24 to move wire holder 144 toward the extracorporeal end of device 10 (and shaft 12-1). Distal ends of engagement wires 146 may be seen removed from holes 152 of receiver 150, but still engaging eyelets 158 and retaining them at the predetermined radial position. Wire guide assists in maintaining engagement wires from not deforming radially outward under any radial forces applied by the (self-expanding) implant 20. Barbs or hooks 160 which are connected to the respective apex of implant 20 may be seen in FIG. 24. These will engage with the vessel wall upon contact with it.

Figure 25:
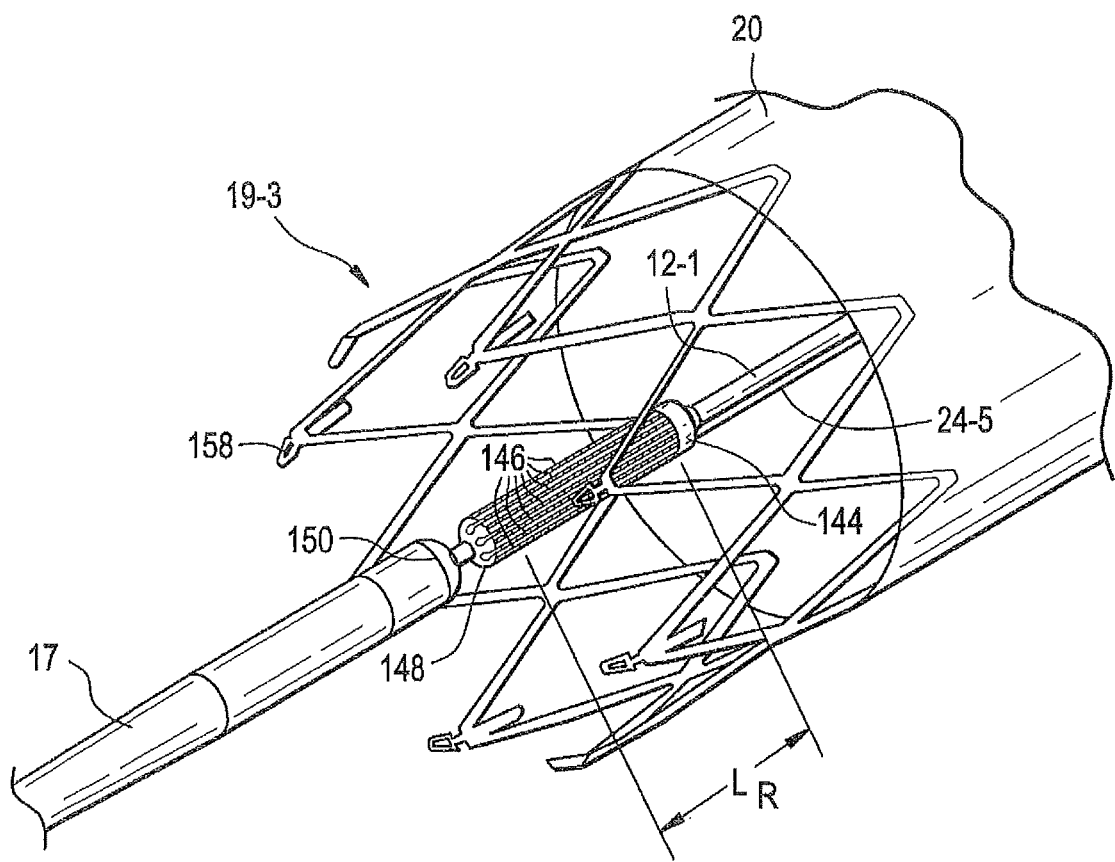
FIG. 25 illustrates the third securement and release mechanism after releasing the cranial end of an implant to an inner member of a delivery device.

FIG. 25 illustrates the embodiment of FIG. 23 after a medical professional has operated apparatus 26 to pull tensile member 24, thereby moving wire holder 144 along shaft 12 a distance, LR, to contact with stop 156 (illustrated in FIG. 22), and withdrawing engagement tensile members 24 from eyelets 158, permitting implant 20 to full expand on its own or be expanded by an expandable member. Full expansion is illustrated in FIG. 25, and the relative diameters of a fully expanded implant 20, which as illustrated as a stent-graft for abdominal aortic aneurismal repair, and the shaft that delivers it to the diseased or desired vascular location.

Figure 26:
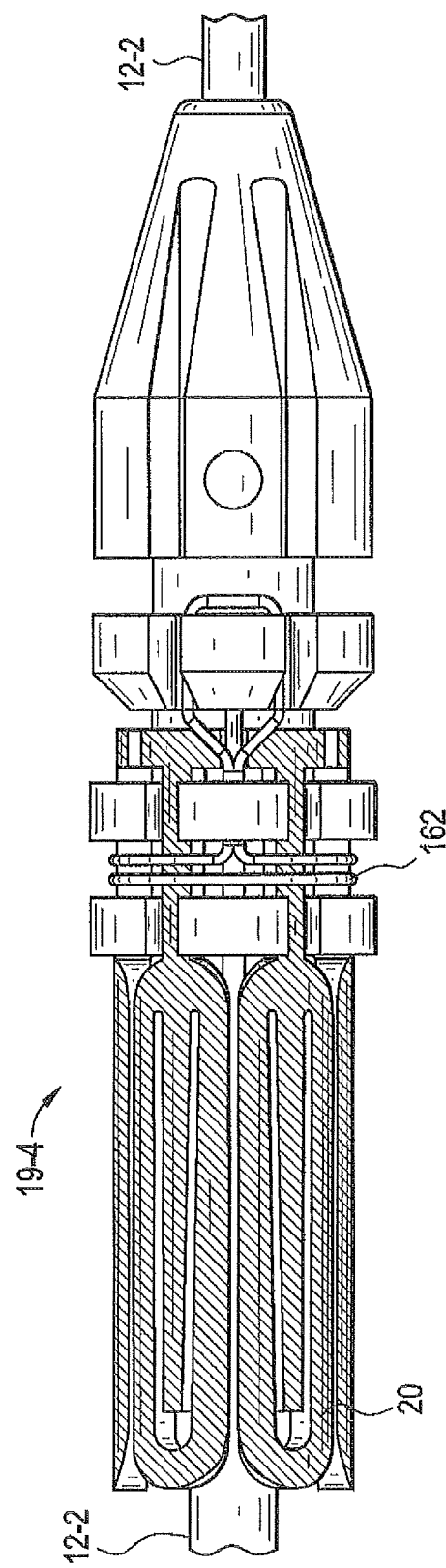
FIG. 26 illustrates a fourth securement and release mechanism to which a tensile member may be attached.
Figure 27:
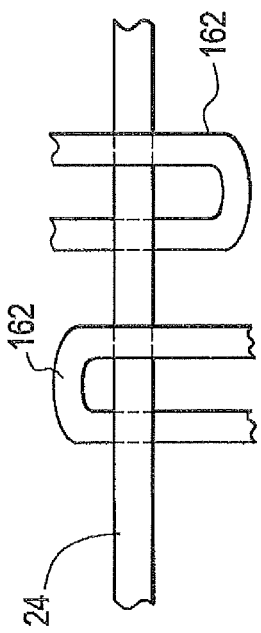
FIG. 27 illustrates how a tensile member may interface with the mechanism of FIG. 26.

FIG. 26 illustrates yet another embodiment 19-4 of a retaining mechanism 19, wherein the release mechanism is only tensile member 24, which is interwoven with retaining wire 162, as illustrated in FIG. 27. Retaining wire 162 encompasses the circumference of the implant 20 at its delivery diameter, and is prevented from expanding by friction from the interweaving with release tensile member 24. Retaining wire 162 is secured to shaft 12-2 at a point along its length so that wire 162 may be withdrawn from the body along with shaft 12-2 after delivery of implant 20.

Figure 28:
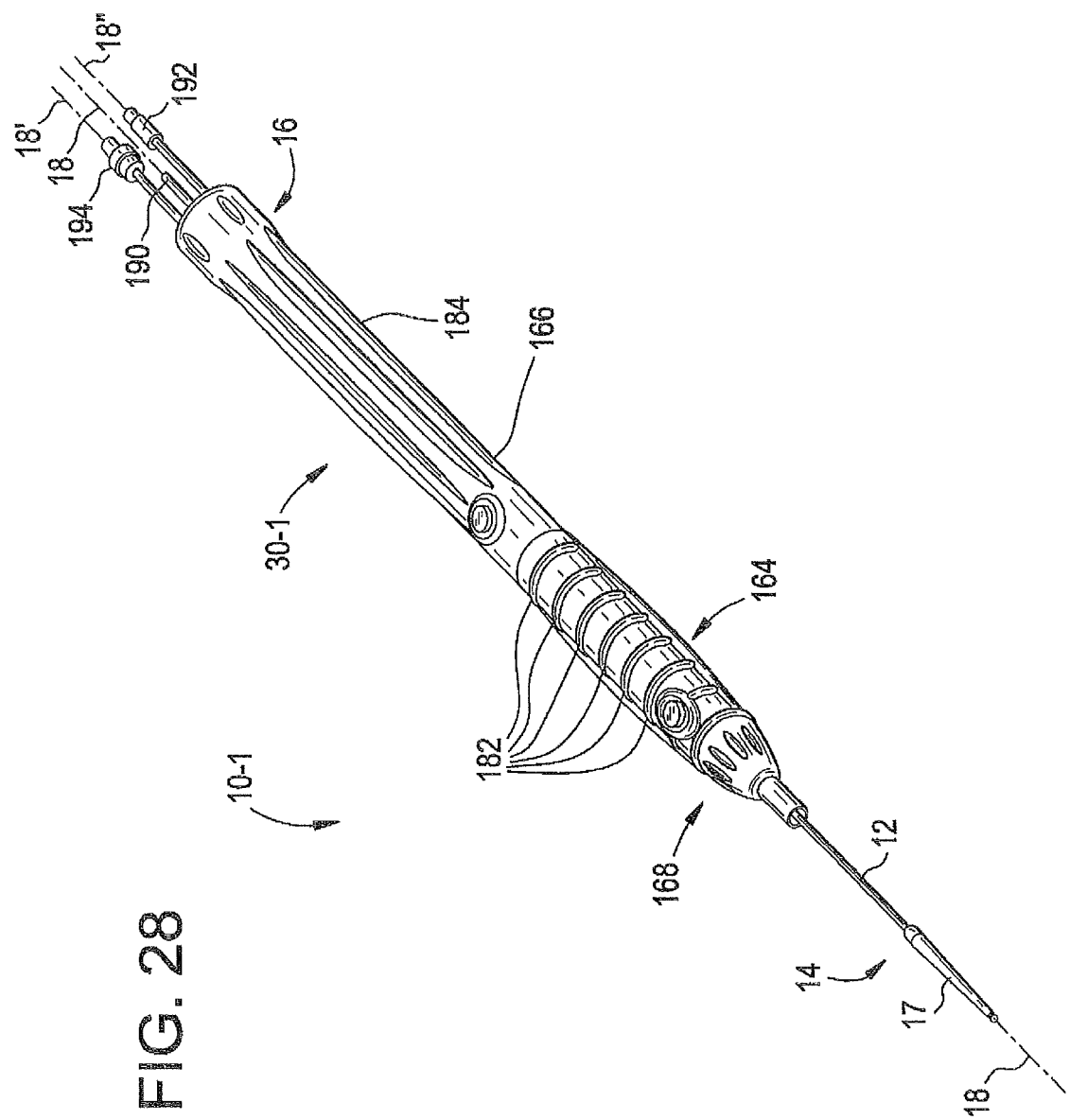
FIG. 28 illustrates an embodiment of a medical device with a handle system for axially retracting a sheath or outer member.

FIG. 28 illustrates device 10-1 and provides greater detail of an embodiment 30-1 of handle system 30 for retracting sheath 28 (not shown here, but in FIG. 1). Handle system 30-1 has a stationary portion 164 rotatably connected to a rotating portion 166. Stationary portion 164 is considered stationary with respect to handle system 30-1 and to the larger delivery catheter system 10-1 of which handle system 30-1 is a part. Stationary portion 164 is movable by the medical professional as part of manipulating the handle system 30 and associated delivery catheter 10-1. Strain relief 168 extend distally form the stationary portion 164 and provides strain relief for delivery catheter 10-1. Inner member of shaft 12 of delivery catheter 10-1 extends distally from handle system 30-1 to a distal tip 17. FIG. 28 illustrates delivery catheter 10-1 much shorter than it would be in most applications, solely for ease of illustration. Delivery catheter 10-1 can be, and in most instances is, considerably longer.

Figure 29:
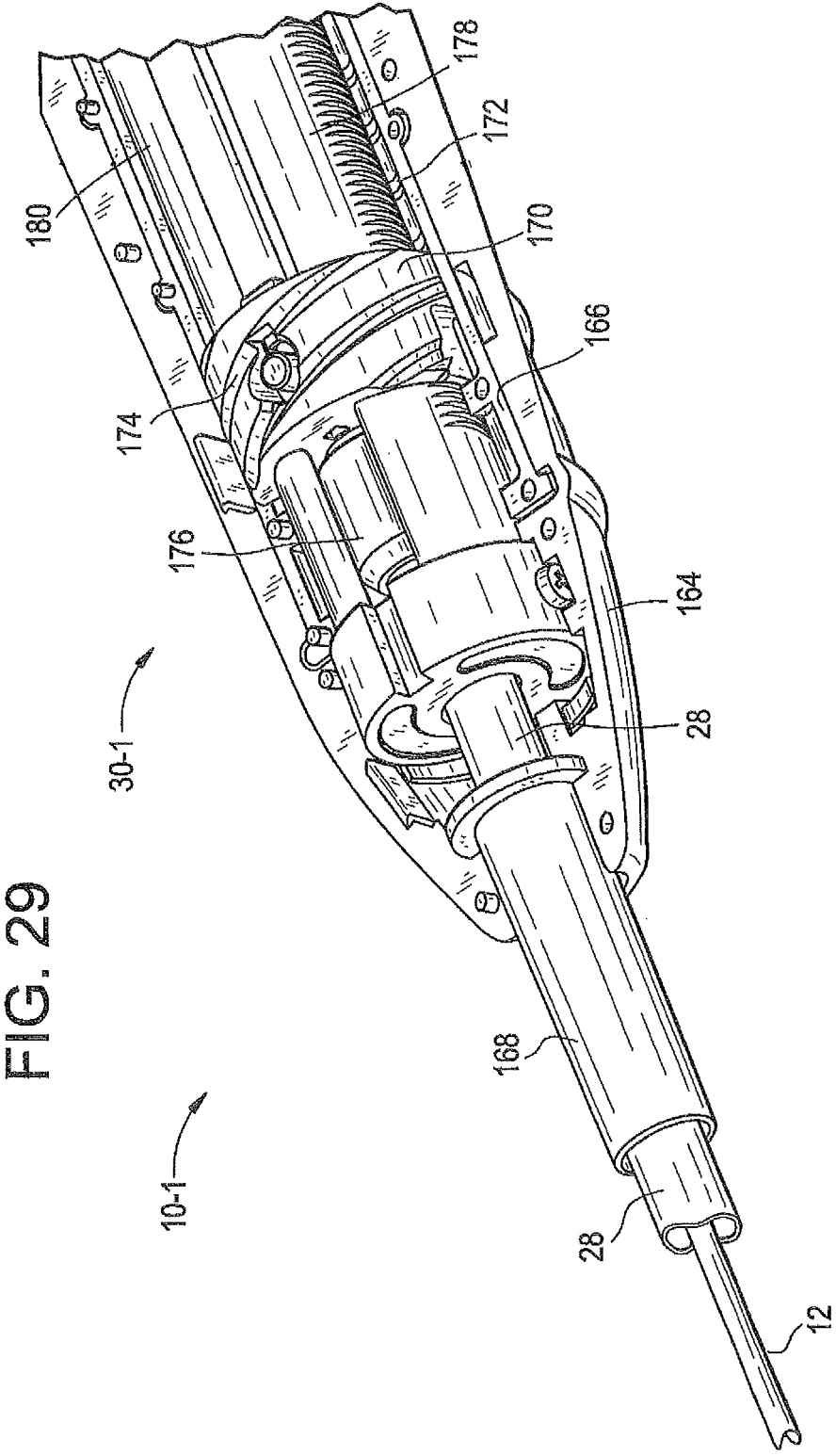
FIG. 29 illustrates a distal portion of the embodiment of FIG. 28.

FIG. 29 illustrates a sectional view of handle system 30-1, and more particularly stationary portion 164. Shown in cutaway view, the outer sheath 28 and inner shaft 12 of delivery catheter 10-1 extend distal of strain relief 168. Rotating portion 166 can extend distal into stationary portion 164, in this case almost to strain relief 168. As will be described, infra, the length of rotating portion 166 limits the axial travel of sheath mount 170, and consequently, the amount by which outer sheath 28 will be axially retracted. Rotating portion 166 has an internal helical thread 172, which mates with an external thread 174 around the exterior of sheath mount 170. In this embodiment, sheath mount 170 is thus rotatably coupled to rotation portion 166, slidably coupled to delivery catheter 10-1, and fixedly coupled, and in fact directly fixed, to outer sheath 28. Outer sheath 28 is secured to sheath mount 170 between a central mounting nipple (not illustrated) and a coaxially mounted tube 176. Sheath mount 170 rides along rails 178 and 180, and has rail bearings for that purpose. It will be apparent with at least the foregoing description that, in general terms, handle system 30-1 is operated to deploy an implant 20 (not shown here, but elsewhere, e.g., in FIG. 1) by rotating rotating portion 166 about the longitudinal axis 18 of delivery catheter 10-1, while holding stationary portion 164 fixed. The rotation of internal thread 172 drives external thread 174 of sheath mount 170 in a proximal direction of handle system 30. Accordingly, outer sheath 28, being secured to sheath mount 170, is retracted proximally solely through translation, without rotation, to expose implant 20 at a distal end of the delivery catheter, and allowing it to expand on its own or be deployed by other means.

To enhance the ability of a medical professional to hold stationary portion 164 fixed with respect to shaft 12 (and apply forces counteracting those applied to rotating portion 166, stationary portion 164 is preferably provided with circumferential ribs 182 as illustrated in FIG. 28.

To enhance the ability of a medical professional to grip rotating portion 166 and rotate it with respect to shaft 12 and stationary portion 164, rotating portion 166 is preferably provided with longitudinal grooves 184 as illustrated in FIG. 28.

Figure 30:
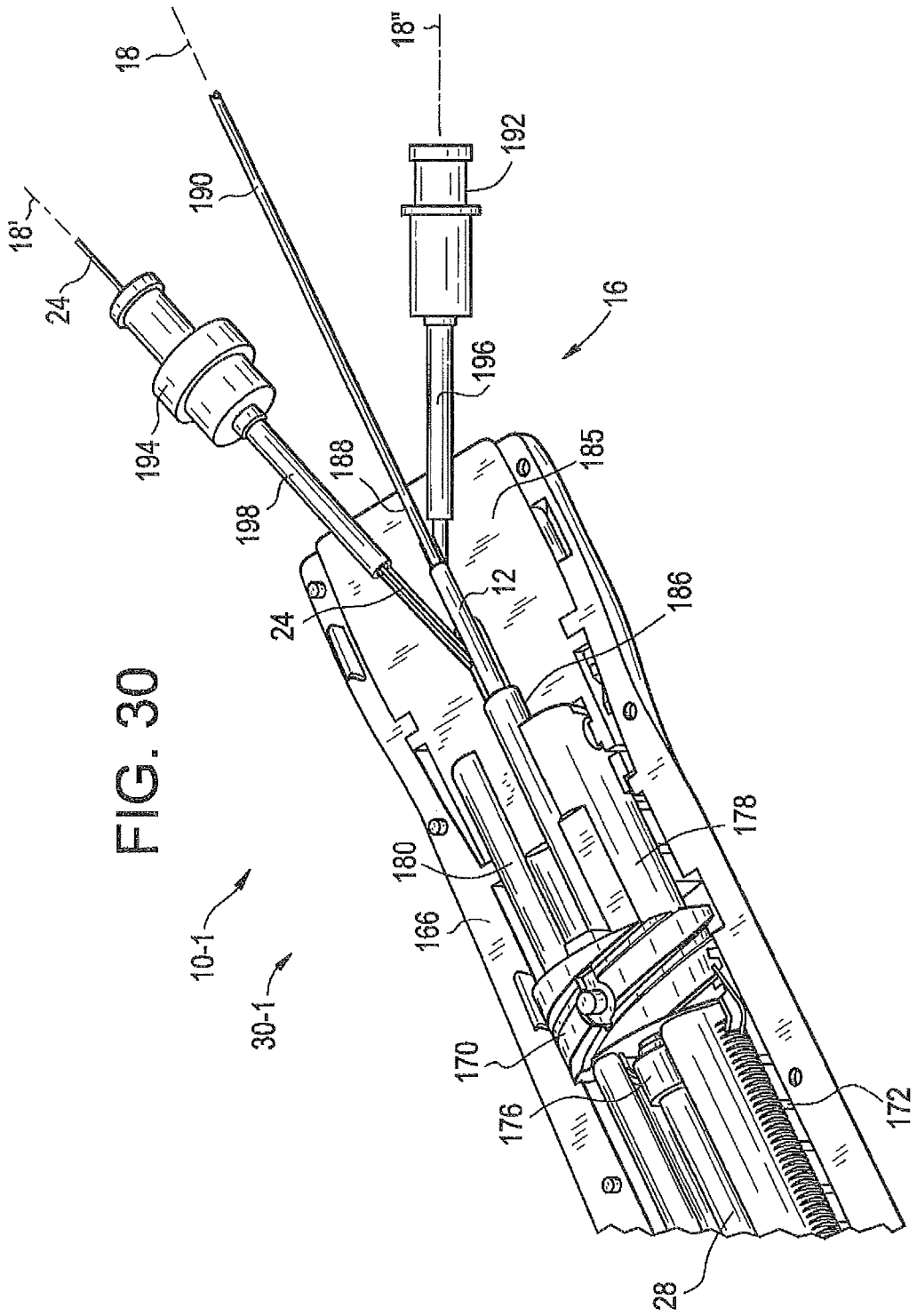
FIG. 30 illustrates a proximal portion of the embodiment of FIG. 28 with the sheath fully retracted.

FIG. 30 illustrates a longitudinal section of handle system 30-1, and more particularly, a proximal end thereof. As illustrated, rotating portion 166 forms a tubular portion with a longitudinal axis coaxial with longitudinal axis 18. Within the proximal end of rotating portion 166, a manifold 185 is rotatably connected. Longitudinal rails 178, 180 extend to manifold 185. Manifold 185 seals to a tube 186, which runs the length of handle system 30-1 to prevent liquids (either supplied to the body from external syringes through luer connectors or blood or other bodily fluids coming from the body) from entering the inner space handle system 30-1 and interfering with the intended interaction of, e.g., internal helical threads 172 and external helical threads 174. Tube 186 defines an annular lumen between itself and the outer surface of inner shaft 15 which extends proximal of tube 186. Manifold 185 also seals to shaft 12. An axial lumen 188 permits a guide wire 190 to pass through the manifold 185 and into inner member of shaft 12. Optionally, one or more luer connectors 192 permit introduction of fluid or agents into manifold 185 and delivery catheter 10-1 by injection with a syringe through tubing 196. Apparatus 26, e.g., any of the embodiments described herein, may be coupled to a luer connector 194, which permits tensile member 24 to exit manifold 185 along a longitudinal axis 18' of connector 194 and tubing 198. As illustrated, luer connector 194 is in a fixed position with a proximal (extracorporeal end) of delivery catheter 10-1.

Figure 31:
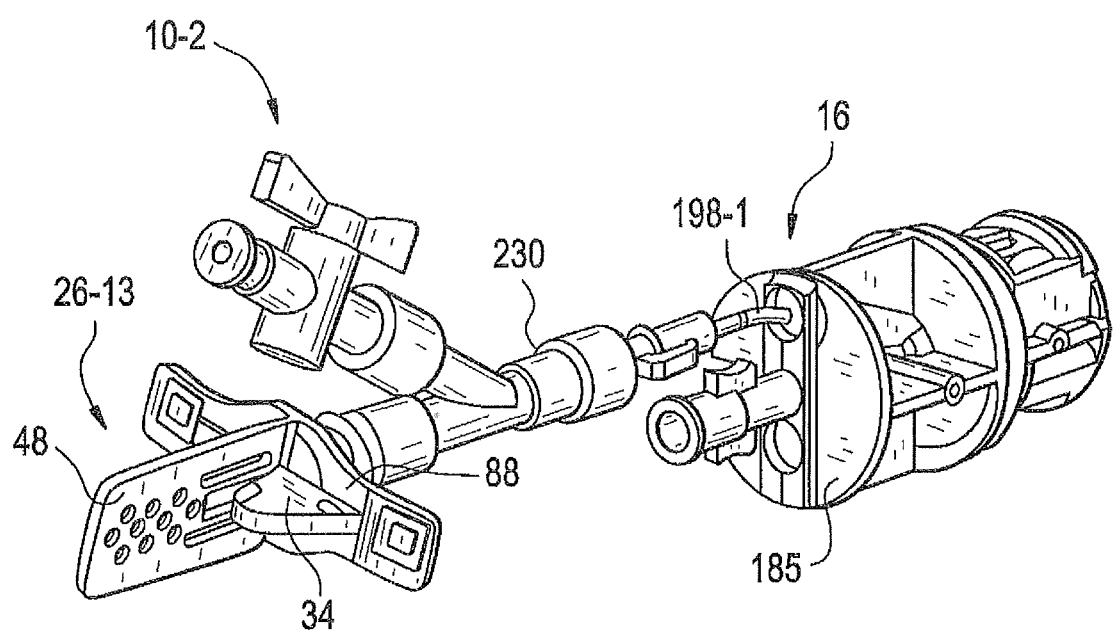
FIG. 31 illustrates another embodiment of an apparatus for pulling a tensile member coupled to a manifold of FIG. 30.

Turning now to FIG. 31, an exemplary coupling between apparatus 26, here a thirteenth embodiment 26-13, and the distal end of device 10-2, here manifold 185. Apparatus 26-13 is coupled to manifold 185 through a number of series connections. Base 88 is removably secured (and connected) to a Y connector 230 through mating threads. The distal end of the Y connector is joined (connected) to a rigid tube 198-1, which is non-removably and sealingly secured (connected) to manifold 185 of device 10-2.

Figure 32A:
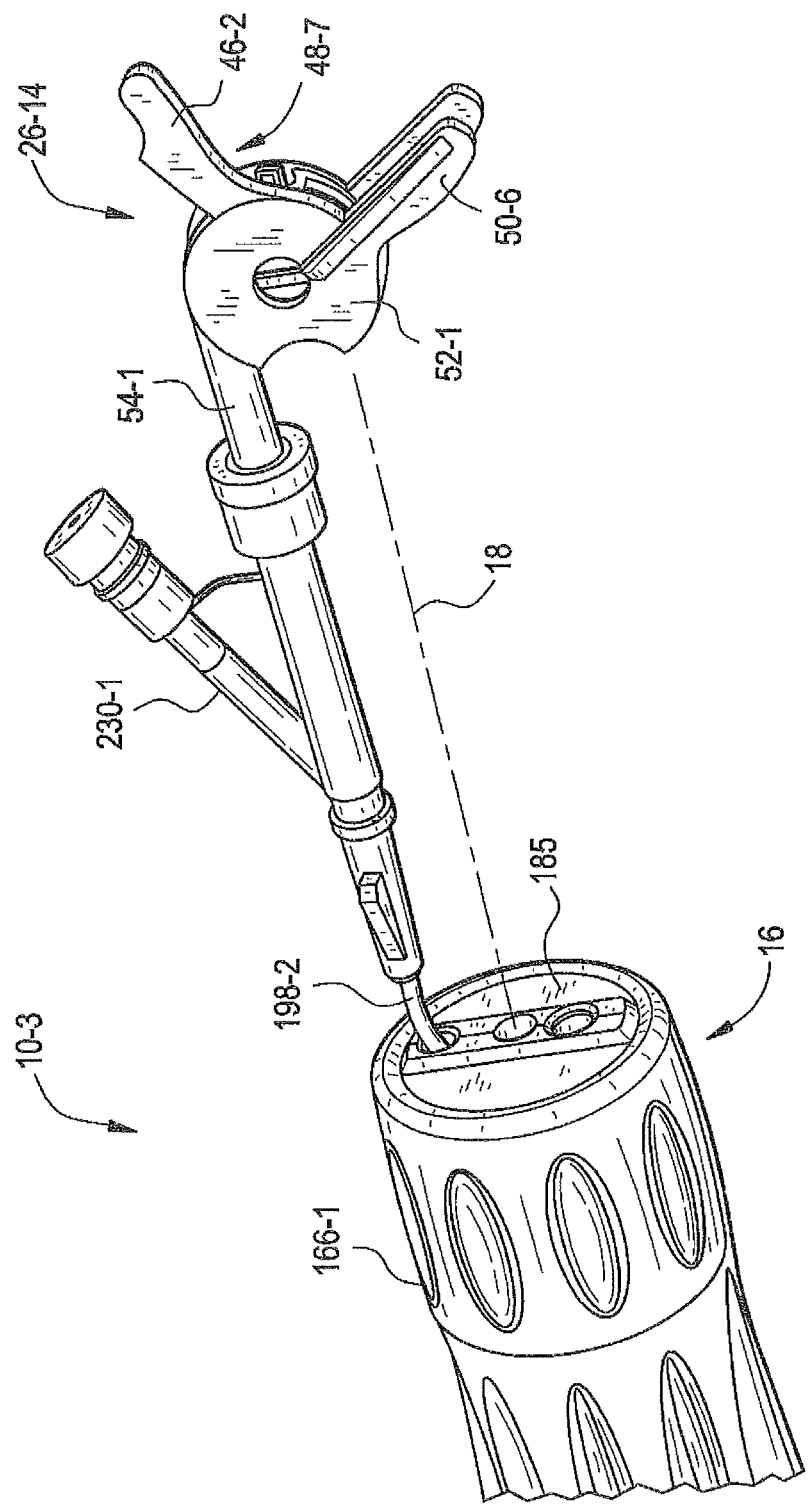
FIG. 32A illustrates yet another embodiment of an apparatus for pulling a tensile member coupled to distal end of a medical device 10.

Turning now to FIG. 32A, it may be desirable to offer a semi-rigid coupling between apparatus 26, e.g., any of its embodiments, including 26-14 as illustrated, and the distal end 16 of a device 10, here, device 10-3. The semi rigid coupling between apparatus 26-14 and manifold 185 of device 10-3 includes rigid tube 54-1 with male threads removably secured (and connected) to rigid Y connector 230-1, which is connected to semi-rigid tubing 198-2. Semi-rigid tubing 198-2 desirably has axial stiffness sufficient to negligibly compress under the actuation load applied via member 46-2 of lever 48-2 of apparatus 26-14 to tensile member 24 (not shown), which is secured to an extracorporeal member of apparatus 26-14, specifically cam 34 (not shown), housed within and rotatably connected to housing 52-1.

Figure 32B:
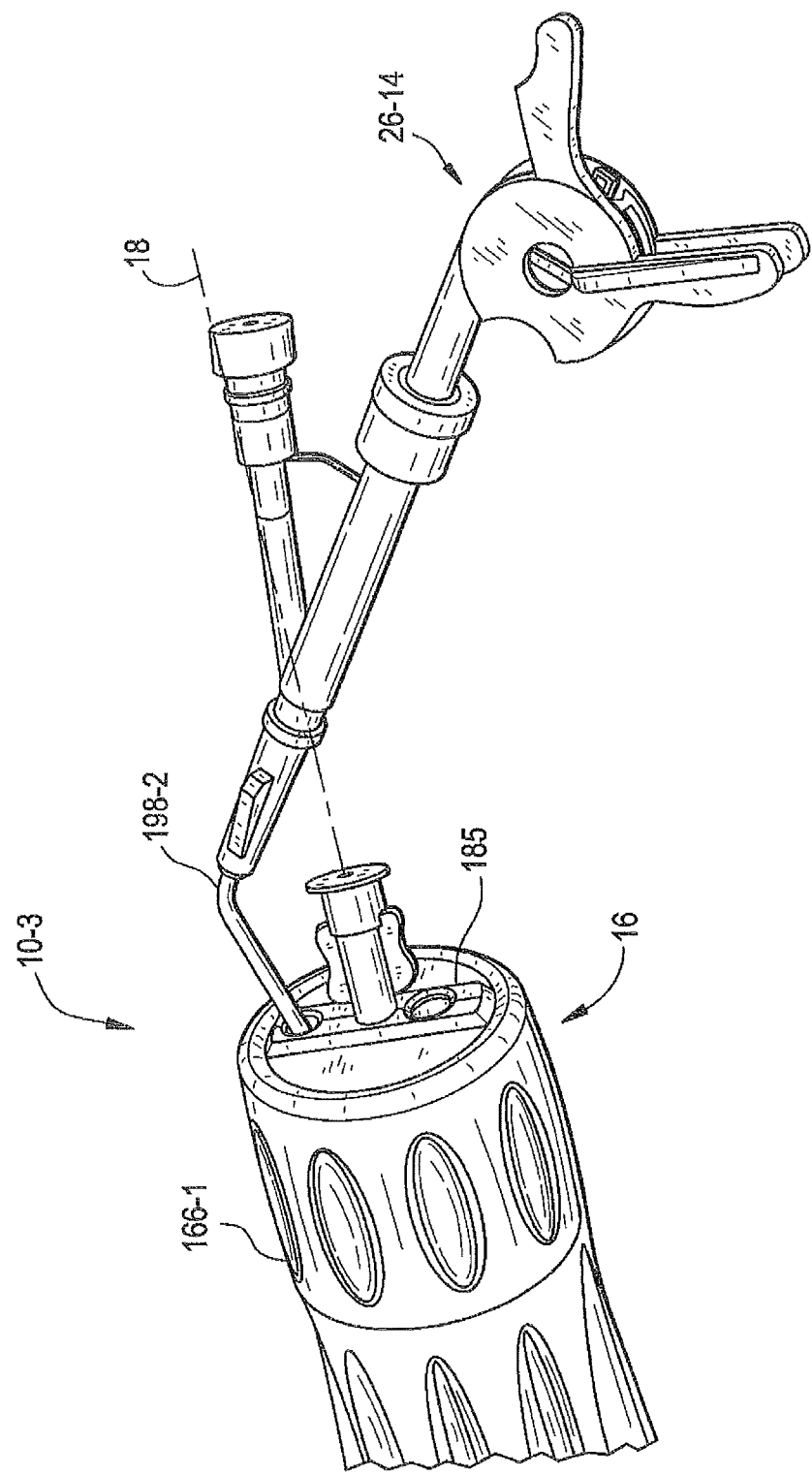
FIG. 32B illustrates the embodiment of FIG. 32A with the flexible tube bent.

In some embodiments, it is anticipated that semi-rigid tubing 198-2 may be bent in any direction up to approximately 90 degrees measured from a line parallel to the longitudinal axis 18 of device 10-3. Such a position approaching 90 degrees bending of semi-rigid tubing 198-2 is illustrates in FIG. 32B. Preferably the bending of semi-rigid tubing 198-2 during use of device 10 negligibly pulls tensile member 24 (not shown) toward distal end 16 of device 10-3 or such non-negligible length is provided for in the movement of tensile member 24 required to actuate a release mechanism in device 10-3.

Aspects of the present invention have been described herein with reference to certain exemplary or preferred embodiments. These embodiments are offered as merely illustrative, not limiting, of the scope of the present invention. Certain alterations or modifications possible include the substitution of selected features from one embodiment to another, the combination of selected features from more than one embodiment, and the elimination of certain features of described embodiments. Other alterations or modifications may be apparent to those skilled in the art in light of instant disclosure without departing from the spirit or scope of the present invention, which is defined solely with reference to the following appended claims.

What is claimed is:

1. An elongated vascular implant delivery device comprising:
   an elongated shaft having a distal end, a proximal end, and a longitudinal axis;
   a release mechanism coupled to a plurality of engagement wires or a plurality of projections and arranged such that the plurality of engagement wires or the plurality of projections (i) extend longitudinally from the release mechanism and (ii) are arranged parallel to or biased toward the elongated shaft both prior to and after disengagement from a distal apex of an implant;
   a lever rotatably coupled to the elongated shaft;
   a tensile member, separate and distinct from the release mechanism, coupled to the release mechanism at a first point along a length of the tensile member and coupled to the lever at a second point along the length of the tensile member and a portion of the tensile member between the first and second points disposed within or alongside the elongated shaft, wherein the first point along the length of the tensile member is a distal tip of the tensile member and the tensile member and the release mechanism are arranged in series;
   a cam configured to receive the portion of the tensile member between the first point and the second point, the cam coupled to the elongated shaft, wherein the lever extends radially from the cam, wherein the second point is on a cylindrical surface of the cam; and
   an axially retractable sheath disposed about at least a length of the elongated shaft and about the implant, the sheath maintaining the implant at a smaller dimension than when deployed, wherein the lever, cam, and tensile member are adapted to cooperate such that rotation of the lever through a prescribed angle with respect to the elongated shaft results in a length of the tensile member between the first point and the second point being brought into contact with the cylindrical surface of the cam, resulting in movement of the release mechanism toward the proximal end of the elongated shaft, and
   wherein the retractable sheath is not retractable by the rotation of the lever through the prescribed angle.

2. The device of claim 1, wherein the cam is rotatably coupled to the elongated shaft.

3. The device of claim 2, wherein the surface of the cam in contact with a length of the tensile member has a constant distance with respect to a pivotal axis about which the cam is rotatable.

4. The device of claim 1, wherein the lever and the cam are integrally formed.

5. The device of claim 1, wherein the surface of the cam in contact with the tensile member is grooved.

6. The device of claim 1, wherein the lever is rotatable about a pivotal axis with respect to the longitudinal axis of the elongated shaft, wherein the pivotal axis is in a fixed position with respect to the longitudinal axis.

7. The device of claim 6, wherein the lever provides a lever arm of at least 2 centimeters in length from the pivotal axis.

8. The device of claim 6, wherein the lever provides a lever arm no more than 15 centimeters in length from the pivotal axis.

9. The device of claim 6, wherein the lever provides a lever arm in length between about 1 and 20 centimeters from the pivotal axis.

10. The device of claim 6, wherein the lever is rotatable about the pivotal axis toward a grip.

11. The device of claim 1, wherein the lever provides a mechanical advantage to pull the tensile member.

12. The device of claim 1, wherein the lever is moveable with a thumb.

13. The device of claim 1, wherein the lever is moveable with one hand.

14. The device of claim 1, wherein the tensile member is coupled to the lever via the cylindrical surface of the cam for securing the tensile member to the lever.

15. The device of claim 1, wherein the tensile member is coupled to the lever via a means for securing the tensile member to the lever, the means for securing comprises a disk around which the tensile member is wrapped and the cylindrical surface of the cam.

16. The device of claim 1, wherein the cam is in a fixed position with respect to a portion of the elongated shaft to which the cam is coupled.

17. The device of claim 1, further comprising a handle rotatable with respect to the longitudinal axis of the elongated shaft, wherein the handle is coupled to the retractable sheath.

18. The device of claim 17, wherein the handle is rotatable about a second pivotal axis, which is parallel to the longitudinal axis of the elongated shaft.

19. The device of claim 1, further comprising:
   a grip coupled to and in a fixed position with respect to a portion of the elongated shaft, the grip adapted to receive forces from one or more digits of a hand.

20. The device of claim 2, wherein the cam is rotatably coupled to the grip.

21. The device of claim 2, wherein the grip projects from a housing within which the cam may rotate.

22. The device of claim 21, wherein the housing removably couples to a proximal end of the elongated shaft.

23. The device of claim 19, wherein the lever and the grip are integrally formed.

24. A method of operating the device of claim 19, the method comprising:
placing a thumb of one hand on the lever;
placing at least one finger of the one hand on the grip;
applying a first force with the thumb of the one hand to the lever; and
applying a second force with the at least one finger on the grip;
whereby the lever rotates about a pivotal axis toward the grip, and the tensile member moves with respect to the elongated shaft.

25. The method of claim 24, wherein the lever rotates 180 or fewer degrees to move the tensile member a predetermined distance with respect to the elongated shaft.

26. The method of claim 24, wherein the lever rotates through a predetermined arc to move the tensile member a predetermined distance with respect to the elongated shaft.

27. An elongated vascular implant delivery device comprising:
an elongated shaft having a distal end, a proximal end, and a longitudinal axis;
a release mechanism coupled to a plurality of engagement wires or a plurality of projections and arranged such that the plurality of engagement wires or the plurality of projections (i) extend longitudinally from the release mechanism and (ii) are arranged parallel to or biased toward the elongated shaft both prior to and after disengagement from a distal apex of an implant;
a lever rotatably coupled to the elongated shaft;
a tensile member, separate and distinct from the release mechanism, coupled to the release mechanism at a first point along a length of the tensile member and coupled to the lever at a second point along the length of the tensile member such that the lever is operable with one hand for pulling the tensile member with respect to the elongated shaft, wherein the first point along the length of the tensile member is a distal tip of the tensile member and the tensile member and the release mechanism are arranged in series;
a cam for a portion of the tensile member between the first point and the second point, the cam coupled to the elongated shaft; and
an axially retractable sheath disposed about at least a length of the elongated shaft and about the implant, the sheath maintaining the implant at a smaller dimension than when deployed, wherein the lever extends radially from the cam and wherein the lever and the cam operates to pull the tensile member at an angle with respect to the elongated shaft, resulting in a length of the tensile member between the first point and the second point being brought into contact with a surface of the cam, resulting in the release mechanism moving toward the proximal end of the elongated shaft, and wherein the retractable sheath is not the tensile member and is not retractable by the rotation of the lever.

28. The device of claim 27, wherein the lever is rotatable about a pivotal axis with respect to the longitudinal axis of the elongated shaft, which pivotal axis is in a fixed position with respect to the longitudinal axis.

29. The device of claim 27, wherein the lever provides a lever arm of at least 2 centimeters in length from a pivotal axis.

30. The device of claim 27, wherein the lever provides a lever arm no more than 15 centimeters in length from a pivotal axis.

31. The device of claim 27, wherein the lever provides a lever arm in length between about 1 and 20 centimeters from a pivotal axis.

32. The device of claim 27, wherein the lever provides a mechanical advantage to pull the tensile member.

33. The device of claim 27, wherein the lever is moveable with a thumb.

34. The device of claim 27, wherein the one hand may be either the left hand or the right hand.

35. The device of claim 27, further comprising a handle rotatable with respect to the longitudinal axis of the elongated shaft, wherein the handle is coupled to the retractable sheath.

36. The device of claim 35, wherein the handle is rotatable about a second pivotal axis, which is parallel to the longitudinal axis of the elongated shaft.

37. The device of claim 27, further including:
a grip coupled to and in a fixed position with respect to a portion of the elongated shaft, the grip adapted to receive forces from one or more digits of the one hand, wherein either the lever or the cam is an extracorporeal member.

38. The device of claim 37, wherein the cam is rotatably coupled to the elongated shaft.

39. The device of claim 37, wherein the cam is rotatably coupled to the grip.

40. The device of claim 37, wherein the grip projects from a housing within which the cam may rotate.

41. The device of claim 40, wherein the housing removably couples to an extracorporeal end of the elongated shaft.

42. The device of claim 37, wherein the lever and the cam are integrally formed.

43. The device of claim 37, wherein the surface of the cam in contact with a length of tensile member has a constant distance with respect to a pivotal axis about with the cam is rotatable.

44. The device of claim 37, wherein the tensile member is coupled to the lever via the surface of the cam for securing the tensile member to the lever.

45. The device of claim 37, wherein the tensile member is coupled to the lever via a means for securing the tensile member to the lever, the means for securing the tensile member comprises a disk around which the tensile member is wrapped and the surface of the cam.

46. The device of claim 37, wherein during operation, the lever rotates about a pivotal axis toward the grip.

47. The device of claim 37, wherein the cam is in a fixed position with respect to a portion of the elongated shaft to which it is coupled.

48. The device of claim 37, wherein the lever and the grip are integrally formed.

49. A method of operating the device of claim 37, the method comprising:
placing a thumb of one hand on the lever;
placing at least one finger of the one hand on the grip;
applying a first force with the thumb of the one hand to the lever; and
applying a second force with the at least one finger on the grip, whereby the lever rotates about a pivotal axis toward the grip, and the tensile member moves with respect to the elongated shaft.

50. The method of claim 49, wherein the lever rotates 180 or fewer degrees to move the tensile member a predetermined distance with respect to the elongated shaft.

51. The method of claim 49, wherein the lever rotates through a predetermined arc to move the tensile member a predetermined distance with respect to the elongated shaft.

* * * * *